US012310698B2

(12) United States Patent
Zeng et al.

(10) Patent No.: US 12,310,698 B2
(45) Date of Patent: May 27, 2025

(54) VOLUMETRIC MULTI-MODAL MICROSCOPY METHODS AND SYSTEMS

(71) Applicant: PROVINCIAL HEALTH SERVICES AUTHORITY, Vancouver (CA)

(72) Inventors: Haishan Zeng, Vancouver (CA); Zhenguo Wu, Vancouver (CA); Harvey Lui, Vancouver (CA); Yunxian Tian, Vancouver (CA)

(73) Assignee: PROVINCIAL HEALTH SERVICES AUTHORITY, Vancouver (CA)

( * ) Notice: Subject to any disclaimer, the term of this patent is extended or adjusted under 35 U.S.C. 154(b) by 981 days.

(21) Appl. No.: 17/309,374

(22) PCT Filed: Nov. 22, 2019

(86) PCT No.: PCT/CA2019/051679
§ 371 (c)(1),
(2) Date: May 21, 2021

(87) PCT Pub. No.: WO2020/102912
PCT Pub. Date: May 28, 2020

(65) Prior Publication Data
US 2022/0015638 A1    Jan. 20, 2022

Related U.S. Application Data

(60) Provisional application No. 62/770,781, filed on Nov. 22, 2018.

(51) Int. Cl.
*A61B 5/00* (2006.01)
*G02B 21/00* (2006.01)
(Continued)

(52) U.S. Cl.
CPC .......... *A61B 5/0075* (2013.01); *A61B 5/0071* (2013.01); *A61B 5/444* (2013.01);
(Continued)

(58) Field of Classification Search
CPC ....... A61B 5/00; A61B 5/0064; A61B 5/0068; A61B 5/0071; A61B 5/0075; A61B 5/444;
(Continued)

(56) References Cited

U.S. PATENT DOCUMENTS

| 11,555,742 B2 * | 1/2023 | Wu ........................... G01J 3/10 |
| 2010/0284024 A1 * | 11/2010 | Vucinic ................ G02B 27/126 |
| | | 250/559.19 |
| 2014/0023993 A1 * | 1/2014 | Zeng ...................... A61B 18/18 |
| | | 606/9 |

OTHER PUBLICATIONS

Chen, K., "A Vertical and Horizontal 3-Axis Hand-Held Confocal Scanner for Skin Imaging Applications", Masters Thesis, Apr. 2015.
(Continued)

*Primary Examiner* — Kent Yip
(74) *Attorney, Agent, or Firm* — Todd A. Rattray; Oyen Wiggs Green & Mutala LLP

(57) ABSTRACT

Methods and apparatus for obtaining 3D imaging of tissue involve scanning a focused laser beam in xz planes to obtain a set of xz plane images spaced apart in a y direction. The xz plane images are processed to correct distortions and motions and combined to provide 3D image data. Surface flatting is optionally performed. Imaging may be performed using a femtosecond (fs) laser beam. Different components of light returning from the tissue may be detected and processed to yield plural co-registered images using different imaging modalities, for example, reflective confocal microscopy (RCM), two photon fluorescence (TPF) and second harmonic generation (SHG).

22 Claims, 8 Drawing Sheets

(51) Int. Cl.
  *G02B 21/36* (2006.01)
  *G02B 27/64* (2006.01)
(52) U.S. Cl.
  CPC ..... *G02B 21/0028* (2013.01); *G02B 21/0048* (2013.01); *G02B 21/006* (2013.01); *G02B 21/0076* (2013.01); *G02B 21/367* (2013.01); *G02B 27/646* (2013.01)
(58) Field of Classification Search
  CPC ............ G02B 21/0028; G02B 21/0048; G02B 21/006; G02B 21/0076; G02B 21/367; G02B 27/646; G02B 21/36; G01N 21/636; G01N 21/6458; G01N 21/65; G01N 21/84
  See application file for complete search history.

(56) References Cited

OTHER PUBLICATIONS

Czekalla, C. et al., "Technical parameters of vertical in vivo multiphoton microscopy: a critical evaluation of the fly scanning method", Laser Physics Letters, vol. 12, No. 8, Jul. 21, 2015.
Thomas, G. et al., "In vivo nonlinear optical imaging to monitor early microscopic changes in a murine cutaneous squamous cell carcinoma model", J. Biophotonics 8, No. 8, 668-680 (2015), published online Oct. 2014.
Sordillo, L. A. et al., "Deep optical imaging of tissue using the second and third near-infrared spectral windows", Journal of Biomedical Optics 19(5), 056004 (May 2014).
Balu, M. et al., "Distinguishing between benign and malignant melanocytic nevi by in vivo multiphoton microscopy", Cancer Res. 2014; 74(10):2688-2697.
Balu, M. et al., "In Vivo Multiphoton Microscopy of Basal Cell Carcinoma", JAMA Dermatology 2015; 151 (10):1068-1074.
Ulrich, M. et al., "In vivo detection of basal cell carcinoma: comparison of a reflectance confocal microscope and a multiphoton tomograph", J Biomed Opt. Jun. 2013; 18(6):61229.
Kurugol, S. et al., "Automated Delineation of Dermal-Epidermal Junction in Reflectance Confocal Microscopy Image Stacks of Human Skin", J Invest Dermatol. Mar. 2015; 135(3):710-717.
Koehler, M. J. et al., "In vivo assessment of human skin aging by multiphoton laser scanning tomography", Opt Lett. Oct. 2006;31(19):2879-81. PubMed PMID: WOS:000240869400021.
Longo, C. et al., "Skin aging: in vivo microscopic assessment of epidermal and dermal changes by means of confocal microscopy", J Am Acad Dermatol. 2013;68(3):e73-e82.
Deka, G. et al., "In vivo wound healing diagnosis with second harmonic and fluorescence lifetime imaging", J Biomed Opt. 2013;18(6):061222.
Calzavara-Pinton, P. et al., "Reflectance Confocal Microscopy for In Vivo Skin Imaging", Photochem Photobiol. 2008;84(6):1421-1430.
Alex, A. et al., "Three-dimensional multiphoton/optical coherence tomography for diagnostic applications in dermatology", J. Biophotonics 2013;6(4):352-362.
Mansoor, H. et al., "Vertical optical sectioning using a magnetically driven confocal microscanner aimed for in vivo clinical imaging", Opt Express. Dec. 2011;19(25):25161-25172.
Qiu, Z. et al., "Targeted vertical cross-sectional imaging with handheld near-infrared dual axes confocal fluorescence endomicroscope", Biomed Opt Express Feb. 2013;4(2):322-330.
Decenciere, E. et al., "Automatic 3D segmentation of multiphoton images: a key step for the quantification of human skin", Skin Research and Technology May 2013;19(2):115-124.
Ono, I. et al., The real-time, three-dimensional analyses of benign and malignant skin tumors by confocal laser scanning microscopy. J Dermatol Sci. 2006;43(2):135-41.
Masters, B. R. et al., "Three-dimensional microscopic biopsy of in vivo human skin:a new technique based on a flexible confocal microscope", Journal of microscopy 1997;185(3):329-38.
Lee, A. et al., "In vivo video rate multiphoton microscopy imaging of human skin", Opt Lett. 2011;36(15):2865-2867.
Wang, H. et al., "Perfectly registered multiphoton and reflectance confocal video rate imaging of in vivo human skin", J Biophotonics. 2013;6(4):305-309.
Sanderson, M. J., "Acquisition of Multiple Real-Time Images for Laser Scanning Microscopy", Microscopy and Analysis 2004:17-24.

\* cited by examiner

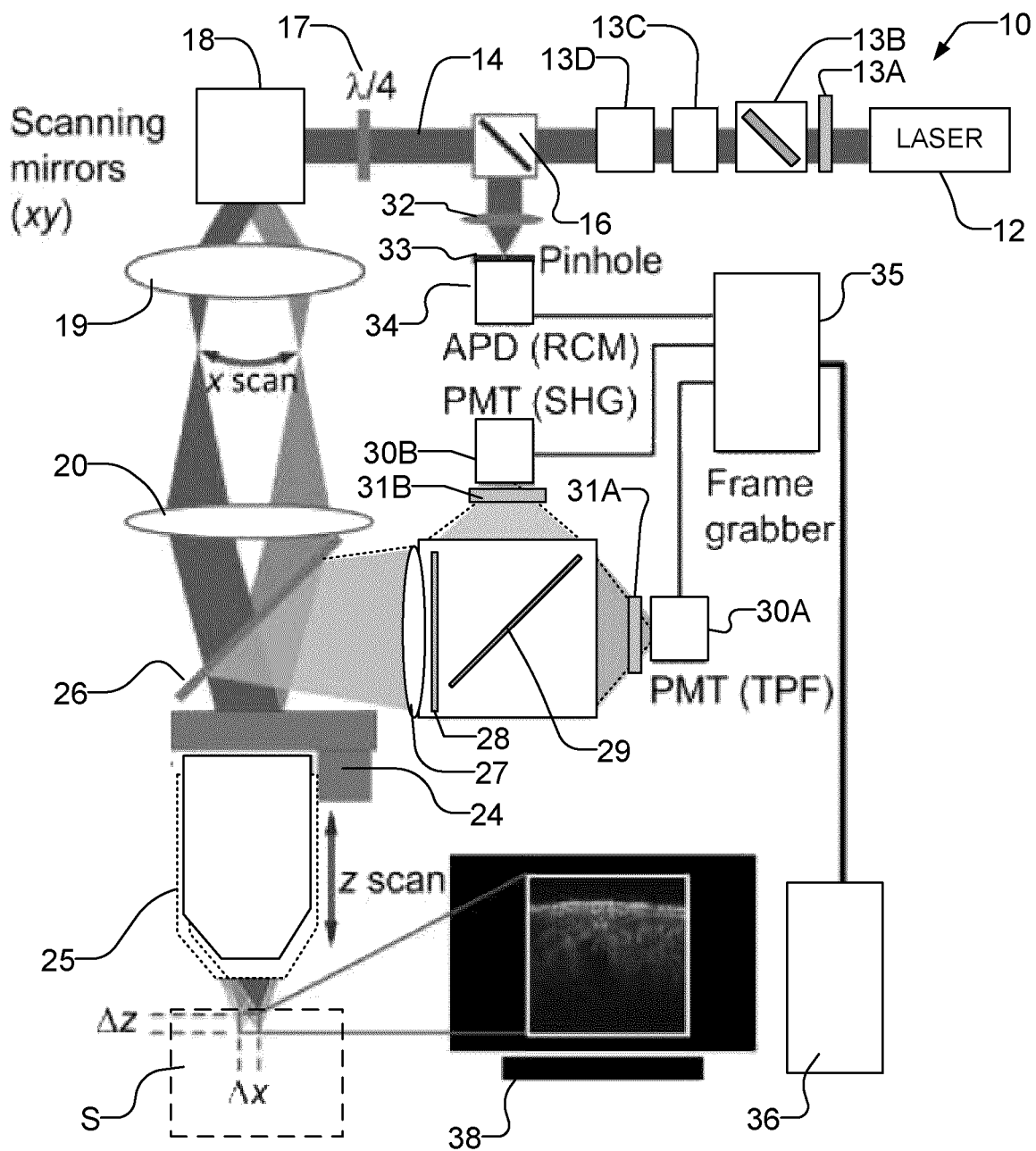
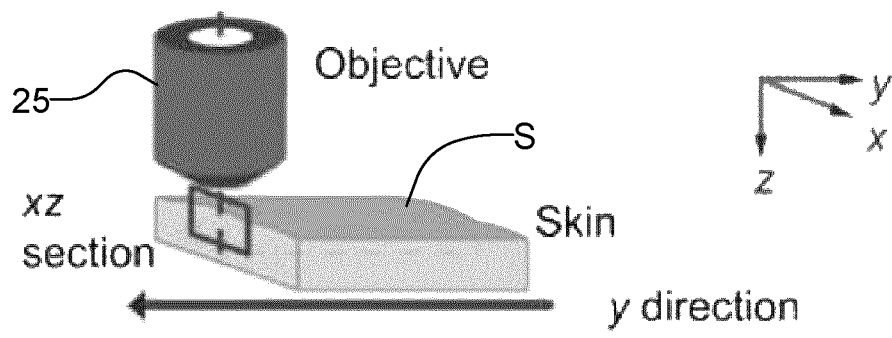
Fig. 1
Fig. 1A

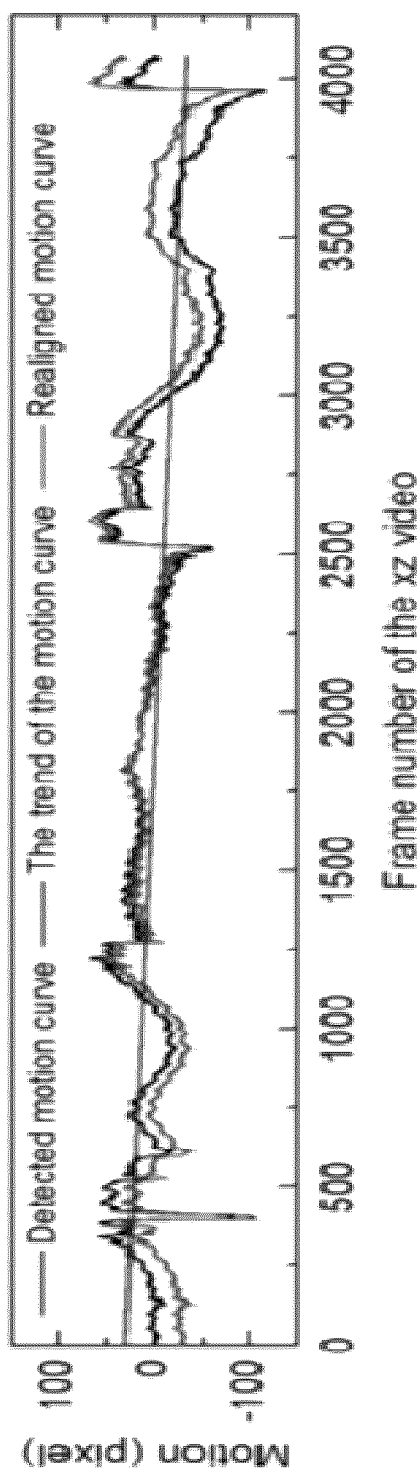
Fig. 8A
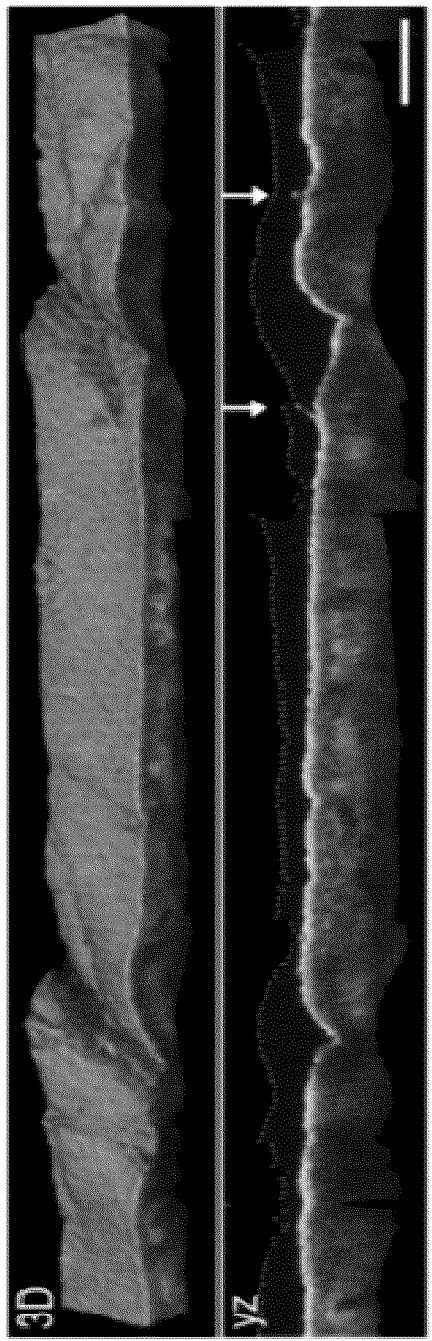
Fig. 8B
Fig. 8C
Fig. 8D

VOLUMETRIC MULTI-MODAL MICROSCOPY METHODS AND SYSTEMS

CROSS-REFERENCE TO RELATED APPLICATIONS

This application claims the benefit under 35 U.S.C. § 119 of U.S. application No. 62/770,781 filed 22 Nov. 2018 and entitled MOTION-TOLERANT, HIGH RESOLUTION, WIDE FIELD VOLUMETRIC OPTICAL BIOPSY THROUGH VERTICAL PLANE TISSUE SCANNING MULTIMODALITY MICROSCOPY which is hereby incorporated herein by reference for all purposes.

FIELD

This invention relates to microscopy. The invention has example application to volumetric microscopy of tissues in-vivo.

BACKGROUND

Diagnosing certain medical conditions such as skin cancer traditionally involves taking a biopsy (tissue sample) and then preparing the tissue sample for microscopic inspection by a pathologist. Tissue samples are generally prepared by fixing, sectioning and staining. Biopsy specimens are typically sectioned vertically so that the pathologist can see cross-sections of tissue layers at different depths in each slide. Microscopic inspection of the tissue samples can reveal cell morphology and other microstructures that are relevant to diagnosis of cancer and other conditions.

Biopsies are invasive procedures that are associated with some risks. In addition biopsies are relatively expensive and it takes time to obtain the results of a biopsy. An alternative to biopsies would be very beneficial. However, biopsies are still recognized as the most accurate way to diagnose skin cancer and various other conditions.

There is a hope that optical noninvasive imaging can be developed to the point that "optical biopsies" could replace at least some conventional biopsies. Ideally some form of optical imaging could noninvasively acquire tissue morphological information such as high resolution, high contrast and large field of view of cell morphology or other microstructures and their interrelationships according to skin depth. One problem in developing suitable noninvasive imaging systems and methods is that skin and other tissues in humans and animals are constantly moving (e.g. due to muscle movement, pulse and respiration). This is especially a problem for optical modalities that require longer image acquisition times.

Reflectance confocal microscopy (RCM) and multiphoton microscopy (MPM) are optical imaging modalities that have application to in vivo skin research. These modalities can provide label-free, subcellular resolution, and good sectioning ability in high scattering tissues. However, RCM and MPM imaging systems tend to provide images corresponding to horizontal (xy plane) sections. Such horizontal plane images are hard to correlate to vertical (xz plane) sections provided by most histology images. Horizontal plane images only contain information from a specific depth. Consequently RCM or MPM horizontal plane images are hard to interpret without special training and, it is hard to measure important morphometric parameters such as tumor depth (e.g. melanoma) or epidermal thickness based on horizontal sections.

Secondly, RCM or MPM images can be adversely affected by movement of tissue being imaged. Such movement can cause image quality to deteriorate and can render already limited depth information inaccurate. These problems are especially severe when the imaging speed is slow. MPM imaging is especially degraded by either a low signal-to-noise ratio at short acquisition times, or motion-induced blurring at long acquisition times. Because of the low excitation efficiency of endogenous fluorophores in skin, to attain a high signal to noise ratio in MPM imaging requires a relatively long pixel dwell time or frame averaging which corresponds to overall slow imaging speed. But slow imaging speed will cause blurring if the tissues being imaged move during the imaging. There have been proposals to address this problem by suppressing movement of the measured subject during imaging but these proposals are often impractical.

Thirdly, the field of view of RCM or MPM images is typically small. Larger fields of view can be obtained by stitching together smaller images. However, any movement of the tissues can affect the images in ways that interfere with stitching the images together and/or make it impossible to be sure that all of the stitched together images are from the same depth.

The following references describe various approaches to imaging:
1. Balu M, Kelly K M, Zachary C B, Harris R M, Krasieva T B, König K, Durkin A J, Tromberg B J. *Distinguishing between benign and malignant melanocytic nevi by in vivo multiphoton microscopy*. Cancer Res. 2014; 74(10): 2688-97.
2. Balu M, Zachary C B, Harris R M, Krasieva T B, König K, Tromberg B J, Kelly K M. *In Vivo Multiphoton Microscopy of Basal Cell Carcinoma*. JAMA dermatology. 2015.
3. Ulrich M, Klemp M, Darvin M E, Konig K, Lademann J, Meinke M C. *In vivo detection of basal cell carcinoma: comparison of a reflectance confocal microscope and a multiphoton tomograph*. J Biomed Opt. 2013 June; 18(6): 61229. PubMed PMID: 23456144.
4. Kurugol S, Kose K, Park B, Dy J G, Brooks D H, Rajadhyaksha M. *Automated delineation of dermal—epidermal junction in reflectance confocal microscopy image stacks of human skin*. J Invest Dermatol. 2014.
5. Koehler M J, Konig K, Elsner P, Buckle R, Kaatz M. *In vivo assessment of human skin aging by multiphoton laser scanning tomography*. Opt Lett. 2006 October; 31(19): 2879-81. PubMed PMID: WOS: 000240869400021.
6. Longo C, Casari A, Beretti F, Cesinaro A M, Pellacani G. *Skin aging: in vivo microscopic assessment of epidermal and dermal changes by means of confocal microscopy*. J Am Acad Dermatol. 2013; 68(3): e73-e82.
7. Deka G, Wu W W, Kao F J. *In vivo wound healing diagnosis with second harmonic and fluorescence lifetime imaging*. J Biomed Opt. 2013; 18(6): 061222
8. Calzavara-Pinton P, Longo C, Venturini M, Sala R, Pellacani G. *Reflectance confocal microscopy for in vivo skin imaging*. Photochem Photobiol. 2008; 84(6): 1421-30.
9. Alex A, Weingast J, Weinigel M, Kellner-Höfer M, Nemecek R, Binder M, Pehamberger H, König K, Drexler W. *Three-dimensional multiphoton/optical coherence tomography for diagnostic applications in dermatology*. J Biophotonics. 2013; 6(4): 352-62.
10. Czekalla C, Schönborn K, Markworth S, Ulrich M, Göppner D, Gollnick H, Röwert-Huber J, Darvin M, Lademann J, Meinke M. *Technical parameters of vertical*

*in vivo multiphoton microscopy: a critical evaluation of the flyscanning method*. Laser Physics Letters. 2015; 12(8): 085602.
11. Thomas G, Voskuilen J, Truong H, Gerritsen H C, Sterenborg H. *In vivo nonlinear optical imaging to monitor early microscopic changes in a murine cutaneous squamous cell carcinoma model*. J Biophotonics. 2014; 8(8).
12. Mansoor H, Zeng H S, Chen K Q, Yu Y Q, Zhao J H, Chiao M. *Vertical optical sectioning using a magnetically driven confocal microscanner aimed for in vivo clinical imaging*. Opt Express. 2011 December; 19(25): 25161-72. PubMed PMID: WOS: 000297702400031.
13. Qiu Z, Liu Z Y, Duan X Y, Khondee S, Joshi B, Mandella M J, Oldham K, Kurabayashi K, Wang T D. *Targeted vertical cross-sectional imaging with handheld near-infrared dual axes confocal fluorescence endomicroscope*. Biomed Opt Express. 2013 February; 4(2): 322-30. PubMed PMID: WOS: 000314806600014.
14. Decenciere E, Tancrede-Bohin E, Dokladal P, Koudoro S, Pena A M, Baldeweck T. *Automatic 3D segmentation of multiphoton images: a key step for the quantification of human skin*. Skin Research and Technology. 2013 May; 19(2): 115-24. PubMed PMID: WOS: 000317937500008.
15. Ono I, Sakemoto A, Ogino J, Kamiya T, Yamashita T, Jimbow K. *The real-time, three-dimensional analyses of benign and malignant skin tumors by confocal laser scanning microscopy*. J Dermatol Sci. 2006; 43(2): 135-41.
16. Masters B, Gonnord G, Corcuff P. *Three-dimensional microscopic biopsy of in vivo human skin: a new technique based on a flexible confocal microscope*. Journal of microscopy. 1997; 185(3): 329-38.
17. Lee A, Wang H, Yu Y, Tang S, Zhao J, Lui H, McLean D I, Zeng H. *In vivo video rate multiphoton microscopy imaging of human skin*. Opt Lett. 2011; 36(15): 2865-7.
18. Wang H, Lee A, Frehlick Z, Lui H, McLean D I, Tang S, Zeng H. *Perfectly registered multiphoton and reflectance confocal video rate imaging of in vivo human skin*. J Biophotonics. 2013; 6(4): 305-9.
19. Sanderson M J. *Acquisition of multiple real-time images for laser scanning microscopy*. Microscopy and analysis. 2004: 17-24.

References 10-13 describe obtaining vertical section RCM and MPM images by methods based on stage-scanning or beam scanning. However, most of the above problems remain. Although the reported vertical section images include depth information, the images suffer from low vertical resolution (determined by the point spread function) as well as slow imaging speed.

References 1, 9, and 14-16 describe making 3D volumetric images by stacking 2D horizontal section (xy plane) images acquired in sequence along a depth (z) direction with a selected step distance. These methods suffer from the same disadvantages discussed above of xy-plane imaging.

Despite the advancements in imaging that have taken place there remains a need for improved imaging modalities, particularly modalities applicable to in vivo imaging of skin and other tissues. There is a particular need for modalities capable of acquiring in vivo tissue optical biopsies that render histological grade imaging while reducing degradation due to motion artifacts and/or depth correlation, improving contrast, and providing increased field of view.

SUMMARY

This invention has a number of aspects that may be applied together or in any subcombinations. These aspects include without limitation:

Methods and apparatus for obtaining volumetric image data for tissues;
Methods and Apparatus for reducing distortions in volumetric image data;
Methods and apparatus for motion compensation in volumetric image data;
Methods and apparatus for flatting skin surfaces in volumetric image data; and
Methods and apparatus for imaging using plural co-registered imaging modalities.

One aspect of the invention provides a method for imaging tissue. The method comprises focusing a beam of light to a focus point, raster scanning the location of the focus point across a field of view in a vertical plane extending generally perpendicular to a surface of the tissue, and collecting and detecting light returning from the focus point to provide a first xz plane image. The location of the focus point is also scanned in a y-direction transverse to the vertical plane to obtain a sequence of additional xz plane images corresponding to vertical planes parallel to and spaced apart in a y-direction from the vertical plane. The first xz plane image and the additional xz plane images constitute a set of xz plane images. The method processes the set of xz plane images to provide volumetric image data for the tissue.

In some embodiments, focusing the beam of light comprises passing the light through an objective and raster scanning the location of the focus point comprises optically scanning the beam in an x direction in coordination with scanning the objective relative to the tissue along a z axis which is generally perpendicular to the x direction and to the surface of the tissue.

In some embodiments, scanning the location of the focus point in the y direction comprises holding the objective fixed in the y direction while moving the tissue in the y direction.

In some embodiments, a range of the scanning in the y direction greater than a range of the scanning in the x direction. For example, the range of scanning in the y direction may be one or more of:
at least three times larger than a range of the scanning in the x direction.
greater than 1 mm;
at least ±2 mm or
at least ±5 mm.

In some embodiments, moving the tissue in the y direction comprises operating a linear motion stage coupled between the objective and a member adhered to a surface of the tissue.

In some embodiments, processing the set of xz plane image frames comprises performing distortion compensation, the distortion compensation comprising monitoring an output of a z-axis position sensor to determine an actual trajectory of the objective during the scanning along the z axis and shifting pixels of the xz image according to the actual trajectory.

In some embodiments, the scanning along the z axis is bidirectional, and the xz plane images include first xz plane images acquired while scanning the objective in a first direction along the z axis and second xz plane images acquired while scanning the objective in a second direction opposed to the first direction along the z axis. In such embodiments the method may include monitoring the output of the z-axis position sensor to determine a first actual trajectory of the objective during the scanning along the z axis in the first direction and a second actual trajectory of the objective during the scanning along the z axis in the second direction and shifting the positions of the pixels of the first xz plane images in the z direction based on the first actual trajectory and shifting the pixels of the second xz plane images in the z direction based on the second actual trajectory.

In some embodiments, processing the set of xz plane image frames comprises performing motion compensation, the motion compensation comprising processing the xz plane images to determine representative z-axis locations of the tissue surface in each of the xz plane images and shifting the pixels of the xz plane images based on the representative z-axis locations.

Shifting the pixels of the xz plane images may be done based on the representative z-axis locations comprises determining differences between the representative z-axis locations for adjacent ones of a sequence of the xz plane images, for each of the xz plane images in the sequence calculating a cumulative difference of the representative z-axis locations relative to a selected one of the xz plane images and shifting the pixels of each of the xz plane images in the sequence by the corresponding cumulative difference.

The representative z-axis location for each of the xz plane images may comprises a position of the tissue surface or another body surface along the z axis averaged across the xz plane image.

In some embodiments, the first xz plane image and the additional xz plane images constitute a first set of xz plane images for a first imaging modality and the method comprises acquiring one or more additional sets of xz plane images, each of the additional sets of xz plane images for a corresponding additional imaging modality and co-registered with the first set of xz plane images and the method comprises shifting the pixels of the xz plane images of the additional sets of xz plane images based on the representative z-axis locations determined for the first set of xz plane images.

In some embodiments, the first imaging modality is RCM. In some embodiments, the additional imaging modality for one of the additional sets of xz plane images is one of TPF, SHG, THG, CARS and SRS.

In some embodiments, processing the set of xz plane image frames comprises performing surface flatting. The surface flatting may comprise processing the xz plane images to yield a 3D profile of the tissue surface; smoothing the 3D profile of the tissue surface; determining offsets corresponding to columns in the xz plane images that extend parallel to the z axis based on the smoothed 3D profile of the tissue surface; and applying the offsets to the xz plane images. Smoothing may, for example, comprise transforming the 3D profile of the surface into a spatial frequency domain (e.g. Fourier domain) by a suitable transformation (e.g. Fourier transform or Fast Fourier Transform (FFT)) and performing filtering in the spatial frequency domain to remove higher spatial frequencies.

In some embodiments, the first xz plane image and the additional xz plane images constitute a first set of xz plane images for a first imaging modality and the method comprises acquiring one or more additional sets of xz plane images, each of the additional sets of xz plane images for a corresponding additional imaging modality and co-registered with the first set of xz plane images and the method comprises applying the offsets to the xz plane images of the additional sets of xz plane images.

For example, the first imaging modality may be RCM. For example, the additional imaging modality for one of the additional sets of xz plane images may be one of TPF, SHG, THG, CARS and SRS.

In some embodiments, collecting and detecting light returning from the focus point comprises splitting the collected light into a plurality of wavelength ranges and separately detecting the portion of the collected light in each of the wavelength ranges.

In some embodiments, collecting and detecting the light returning from the focus point comprises: descanning and directing light having a wavelength that is the same as a wavelength of the beam of light to a first light detector; and directing light having a wavelength that is shorter than a wavelength of the beam of light to a second light detector.

In some embodiments, collecting and detecting the light returning from the focus point comprises: by a first wavelength selective element, redirecting a portion of the returning light having a wavelength that is shorter than a wavelength of the beam of light to a second wavelength selective element; descanning and directing the remaining returning light to a first light detector; and by the second wavelength selective element splitting the portion of the returning light into first and second parts; and directing the first part to a second light detector and directing the second part to a third light detector.

In some embodiments, the beam of light comprises a femtosecond laser beam having a wavelength in the red or infrared. For example, the wavelength may be in in the range of 400 nm to 2300 nm or in the range of 700 nm to 1000 nm.

In some embodiments, the method comprises separating and detecting a plurality of components of the light returning from the focus point using a plurality of different light detectors and processing output signals from the plurality of light detectors to provide a plurality of co-registered images according to plural imaging modalities. The plural imaging modalities may, for example comprise two or more selected from RCM, TPF, SHG, THG, CARS and SRS.

In some embodiments the method comprises operating a frame grabber in coordination with the raster scanning the location of the focus point to assemble each of the xz plane images as a frame.

In some embodiments, the method comprises dividing the set of xz plane images into a sequence of groups of N sequential ones of the xz plane images, combining the N sequential ones of the xz plane images in each of the groups to yield a combined xz plane image and performing the processing on the combined xz plane images. The combining may, for example comprise averaging.

Another aspect of the invention provides apparatus for imaging. The apparatus may, for example, be applied to image tissue (e.g. for optical biopsies). The apparatus comprises: some or all of a laser light source operative to emit a beam of light; an objective arranged to receive and focus the beam of light to a focus point; a scanner unit in an optical path between the laser light source and the objective, the scanner unit operative to redirect the beam of light and thereby cause the focus point to scan in an x direction; a z-axis scanner operative to move the objective in a z direction parallel to an optical axis of the objective, a first light detector arranged to receive light returning through the objective from the focus point and to generate an output signal representing an intensity of the light returning, a tissue stabilizing mechanism coupled to the objective by way of a movable stage operative to move tissue relative to the objective in a y direction that is transverse relative to the x direction, a controller configured to generate coordinated driving signals for the scanner unit and the z-axis scanner to cause the focus point to be raster scanned in an xz plane and control signals for the movable stage to cause the focus point to be scanned in the y direction, a frame grabber operative to monitor the output signal in coordination with the raster scanning of the focus point to build a first series of xz image frames, and a data processor connected to receive the xz image frames and configured to process the xz image frames to provide volumetric image data for a volume scanned by the focus point.

In some embodiments, a range of the scanning in the y direction is larger than a range of the scanning in the x direction. For example, the range of scanning in the y direction may be one or more of:
- at least three times larger (i.e. larger by a factor of at least three) than a range of the scanning in the x direction.
- greater than 1 mm;
- at least ±2 mm; or
- at least ±5 mm.

Some embodiments comprise a first wavelength selective element in the optical path between the scanning unit and the objective, the first wavelength selective element arranged to redirect a portion of the returning light having a wavelength that is shorter than a wavelength of the beam of light out of the beam and a second light detector arranged to detect light from the portion of the returning light. Some such embodiments also comprise a second wavelength selective element arranged to receive the portion of the returning light redirected by the first wavelength selective element and to split the portion of the returning light into first and second parts; and a third light detector arranged to detect light of the third part wherein the second light detector is arranged to detect light of the second part.

In some embodiments an output of the third light detector is connected to the frame grabber and the frame grabber is configured to build a third series of xz image frames co-registered with the first series of xz image frames and/or an output of the second light detector is connected to the frame grabber and the frame grabber is configured to build a second series of xz image frames co-registered with the first series of xz image frames.

Some embodiments comprise a z-axis position sensor operative to output a signal indicative of a displacement of the objective in the z direction. In such embodiments processing the set of xz plane image frames may comprise performing distortion compensation, the distortion compensation comprising monitoring the output of the z-axis position sensor to determine an actual trajectory of the objective during the scanning along the z axis and shifting pixels of the xz image frames according to the actual trajectory.

In some embodiments the scanning along the z axis is bidirectional. In such embodiments the xz plane image frames include first xz plane image frames acquired while scanning the objective in a first direction along the z axis and second xz plane image frames acquired while scanning the objective in a second direction opposed to the first direction along the z axis. In such embodiments the data processor may be configured to monitor the output of the z-axis position sensor to determine a first actual trajectory of the objective during the scanning along the z axis in the first direction and a second actual trajectory of the objective during the scanning along the z axis in the second direction and to shift the positions of the pixels of the first xz plane image frames in the z direction based on the first actual trajectory and to shift the pixels of the second xz plane images in the z direction based on the second actual trajectory.

In some embodiments the data processor is configured to perform motion compensation. The motion compensation may comprise processing the xz plane image frames to determine representative z-axis locations of a tissue surface in each of the xz plane images and to shift the pixels of the xz plane images based on the representative z-axis locations. For example, the data processor may be configured to determine differences between the representative z-axis locations for adjacent ones of a sequence of the xz plane image frames, for each of the xz plane image frames in the sequence calculating a cumulative difference of the representative z-axis locations relative to a selected one of the xz plane images and shifting the pixels of each of the xz plane image frames in the sequence by the corresponding cumulative difference.

In some embodiments the data processor is configured to divide the first series of xz image frames into a sequence of groups of N sequential ones of the xz plane images frames, combine (e.g. by averaging) the N sequential ones of the xz plane image frames in each of the groups to yield a combined xz plane image frame and perform the processing on the combined xz plane image frames.

In some embodiments the laser light source comprises a pulsed laser, for example a femtosecond laser. In some embodiments the light emitted by the laser light source has a wavelength in the range of 400 nm to 2300 nm or 700 nm to 1000 nm.

The apparatus may, for example, be configured to perform plural co-registered imaging modalities selected from RCM, TPF, SHG, THG, CARS and SRS.

Another aspect of the invention provides a method for motion compensating image data. The method comprises obtaining a sequence comprising plural vertical plane images of a tissue comprising a body surface, the plural vertical plane images each including a portion comprising a cross section of the body surface that extends across the vertical plane image; processing the vertical plane images to generate representative locations of the body surface in each of the vertical plane images; and shifting pixels of the vertical plane images in a vertical direction based on the representative locations. The method may include computing differences between the representative locations for pairs of the vertical plane images that are adjacent in the sequence and summing the differences to determine cumulative differences between the representative location for a first one of the vertical plane images and the reference locations for a plurality of other ones of the vertical plane images.

The methods and apparatus described herein have example application to skin disease diagnosis and treatment monitoring and in vivo skin research.

Further aspects and example embodiments are illustrated in the accompanying drawings and/or described in the following description.

BRIEF DESCRIPTION OF THE DRAWINGS

The accompanying drawings illustrate non-limiting example embodiments of the invention.

FIG. 1 is a schematic illustration of apparatus according to an example embodiment.

FIG. 1A illustrates the orientation of an xz plane.

FIGS. 7A and 7B are two adjacent example RCM xz plane image frames. FIG. 7C is a graph showing detected surface positions in the z direction of the frames shown in FIGS. 7A and 7B. FIG. 7D is a curve representing the differences of position of the detected surface between the frames of FIGS. 7A and 7B. FIG. 7E is a frequency histogram of the curve of FIG. 7D showing the mode and a selection window. FIG. 7F shows the surface position difference curve with outliers removed and an average value of the difference.

FIGS. 8A to 8D illustrate motion detection and correction of an example volume. FIG. 8A shows example motion curves. FIG. 8B is a 3D image of the motion corrected volume. FIG. 8C is a vertical plane image of the motion corrected volume.

FIG. 8D is a vertical plane image of the raw volume before motion correction corresponding to FIG. 8C. The black and white arrows point to protruding structures on the skin surface. The scale bar indicates 200 μm.

DETAILED DESCRIPTION

Figure 2:
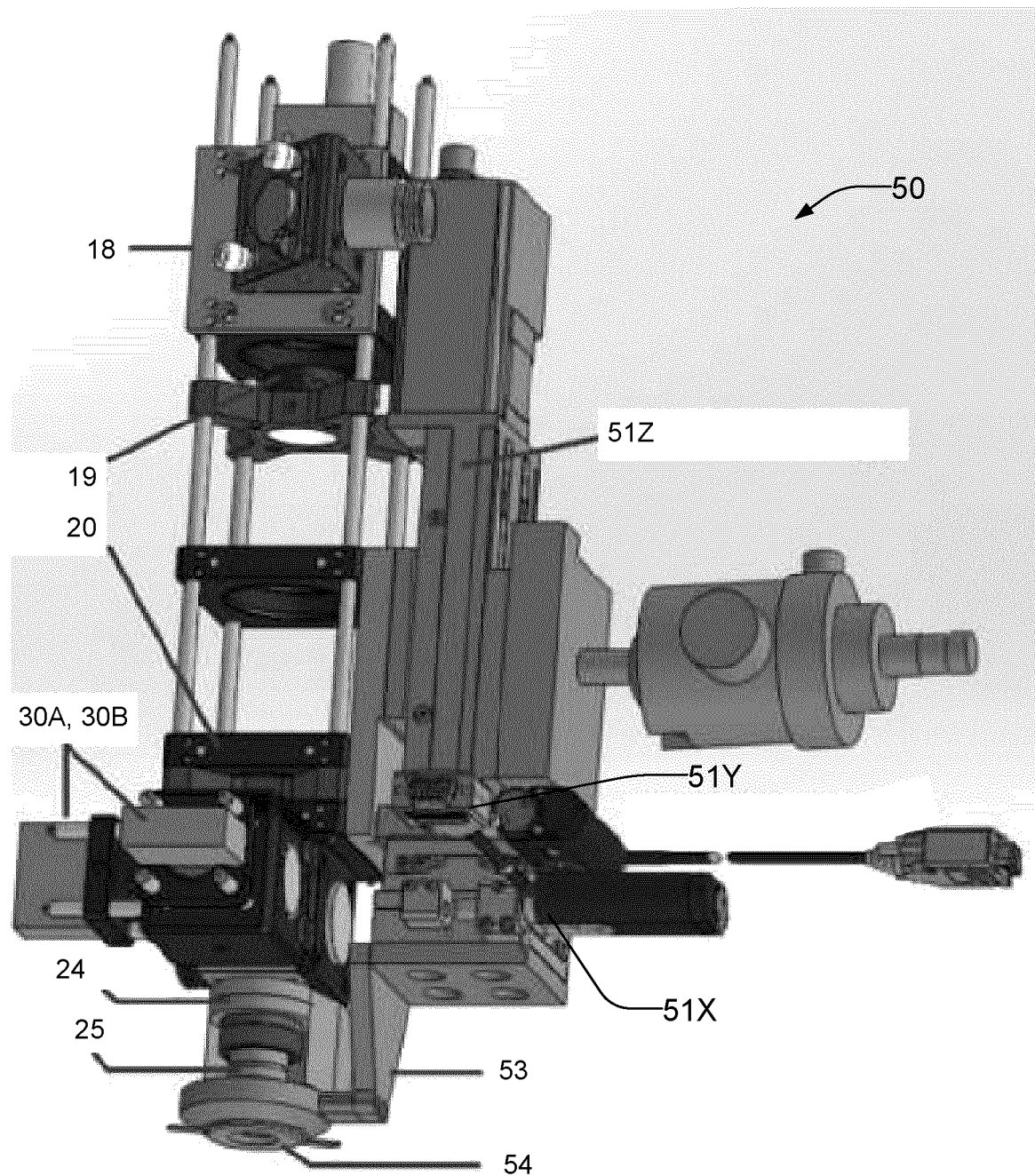
FIG. 2 is a perspective view of an example imaging head.

Throughout the following description, specific details are set forth in order to provide a more thorough understanding of the invention. However, the invention may be practiced without these particulars. In other instances, well known elements have not been shown or described in detail to avoid unnecessarily obscuring the invention. Accordingly, the specification and drawings are to be regarded in an illustrative, rather than a restrictive sense.

One aspect of the invention provides a 3D volumetric multimodal microscopy optical biopsy technique that incorporates fast vertical plane imaging. Here, unless otherwise stated or implied:
 "vertical" is referenced to the surface of a tissue being imaged.
 a "vertical plane" is a plane that is at least generally perpendicular to the tissue surface.
 "horizontal" is also referenced to the tissue surface.
 a "horizontal plane" is a plane that is at least generally parallel to the tissue surface.

The axes x, y and z may be used to describe directions and planes. In this description, unless otherwise stated or implied:
 the z axis is oriented normal to the tissue surface;
 the x and y axes are each oriented parallel to the tissue surface (and are each normal to the z axis);
 when a plane is described with reference to two axes (e.g. xz plane or xy plane) then the plane is a plane that is parallel to both of the two axes. For example, an xy plane can also be described as a horizontal plane and is at least generally parallel to the tissue surface. An xz plane is an example of a vertical plane.

The technique acquires plural vertical plane (x-z plane) tissue scanning images that are spaced apart in a horizontal direction (along the y-axis). The technique is applicable to optical imaging modalities including RCM and MPM.

Once a volumetric data set has been prepared, the data may be viewed in any plane. For example, the data may be viewed in xz planes to observe low power histology like tissue structure information and/or the data may be viewed in any xy plane to observe high resolution cellular morphology and/or the data may be viewed in arbitrary planes. Further, the data allows display of any structures of interest and their interrelationships with one another and with their surroundings in three dimensions.

A system that incorporates some or all of the present technology may apply any suitable imaging modality. Optionally and advantageously a system may apply plural imaging modalities. The system may provide automatic co-registration of the plural modalities. The modalities may, for example, include one or more of:
 RCM
 two photon fluorescence (TPF);
 second harmonic generation (SHG);
 third harmonic generation (THG);
 coherent anti-Stokes Raman scattering (CARS);
 stimulated Raman scattering (SRS)
 any other modality based on laser scanning microscopy.

Some embodiments combine RCM together with one, two or more other modalities that provide enhanced contrast for different constituents of tissue. RCM is based on elastic scattering due to refractive index variation within tissue; TPF relies on endogenous tissue fluorophores including keratin, NADH, melanin, FAD, and elastin; and SHG is a separate optical mode that is due to second harmonic signals which arise primarily from collagen in the skin.

An example implementation of the present technology is provided by the imaging system 10 illustrated schematically in FIG. 1. System 10 can be operated to acquire and co-register images from three microscopy imaging modalities to provide complimentary tissue contrasts. For example, system 10 is operable to perform imaging in RCM and two MPM modes TPF and SHG.

In system 10 a single light source (laser 12) is used for plural imaging modalities. This facilitates co-registration of images acquired using the different modalities.

In system 10 a laser 12 emits a laser beam 14. Laser 12 is a pulsed laser that emits very short pulses of light of relatively high power. For example, 12 may be a femtosecond laser. The light in beam 14 may be in the red, near infrared or infrared spectrum. For example, beam 14 may have a wavelength in the range of about 400 to 2300 nm or the range of about 700 to 1000 nm. In an example implementation, beam 14 has a wavelength of 880 nm or 785 nm or 735 nm. In a prototype embodiment laser 12 was an 80 MHz Ti: sapphire femtosecond laser (Chameleon, Coherent Inc., Santa Clara, California) having a wavelength tunable in the range of 720-950 nm.

Laser beam 14 is conditioned. In the illustrated implementation the conditioning adjusts power of beam 14, adjusts pulses to pre-compensate for dispersion and expands and collimates beam 14. Beam 14 passes through a half wave plate 13A and a polarizer 13B (e.g. a polarizing beam splitter). Half-wave plate 13A may be rotated relative to polarizer 13B to adjust the power of laser beam 14 illuminating a sample. For example, half-wave plate 15 may be rotatable by a motor or other actuator (not shown) to adjust power of beam 14. The pulse width of beam 14 is pre-compensated by compensator 13C which may, for example comprise a prism pair. Beam 14 is then expanded and collimated by beam expander 13D.

The conditioned beam 14 passes through a polarizing beamsplitter 16 and a quarter wave plate 17 which are used for RCM as described below before reaching a scanning unit 18. Scanning unit 18 is operable to scan beam 14 in at least one dimension (x). Scanning unit 18 may optionally be operable to scan beam 14 in two dimensions (x, y). Scanning unit 18 may, for example, be provided by scanning mirrors arranged to provide 1D or 2D scanning.

In some embodiments the direction scanned by scanning unit 18 is adjustable. Such adjustment may be used to adjust the direction of scanning by scanning unit 18 to be transverse to another scanning direction. Rotation of the direction of scan by scanning unit 18 may be achieved by physically rotating scanning unit 18 and/or by providing a scanning unit 18 which includes two scanning mechanisms which are each operative to scan beam 14 and adjusting magnitudes and relative phases of driving signals for the two scanning mechanisms. The two scanning mechanisms may, for example, each comprise a resonant scanning mirror and may be oriented to scan beam 14 in perpendicular directions.

In the prototype embodiment, scanner 18 is provided by an 8 kHz resonant scanning mirror which scans beam 14 in a direction that is here defined as the x direction and a second scanner mirror (a galvo scanner) operable to scan beam 14 in a direction that is perpendicular to the x direction.

Beam 14 is relayed to the rear aperture of an objective 25. In the illustrated implementation beam 14 is relayed by lenses 19 and 20. Objective 25 is supported by a z-scanner 24 which scans a focus point of objective 25 in a z direction. The z direction may correspond to the depth direction in a sample and may be orthogonal to the x (or x and y) scanning direction(s) of scanner 18.

In the prototype embodiment objective 25 is a 60X (NA=1.0) water-immersion objective (LUMPLFLN60X/W, Olympus Canada, Markham, Ontario). In the prototype embodiment, z scanner 24 is provided by a piezoelectric positioner (MIPOS 500, Piezosystem Jena GmbH, Jena, Germany). The piezoelectric positioner was controlled by a controller unit (NV 40/1CLE, Piezosystem Jena GmbH, Jena) which has a bandwidth of about 10 Hz for the piezoelectric positioner (capacitance of 21 µF). As described elsewhere herein the piezoelectric scanner was driven by a sinusoidal voltage waveform generated by a data acquisition card (NI USB-6343, National Instruments, Inc.) and provided to the controller to drive z-axis positioner 24 to scan the spot at which beam 14 is focused by objective 25 in the z direction.

In system 12, RCM is performed by capturing light of beam 14 that has been reflected from the sample. This reflected light has the same wavelength as the light of incident beam 14. The reflected light ("reflectance signal") is descanned by scanner 18. After passing back through quarter-wave plate 17 the polarization of the reflectance signal is such that the reflectance signal is redirected by polarizing beam splitter 16 and is focused onto a light detector 34. Light detector 34 may, for example, comprise an avalanche photodiode.

In the illustrated implementation a lens 32 focuses the light of the reflectance signal onto a pinhole 33. Light passing through pinhole 33 is detected by light detector 34. Most light reflected from points in the sample away from the focus of objective lens 25 is rejected by pinhole 33.

In the prototype embodiment light detector 34 is provided by an avalanche photodiode (APD) module (C10508, Hamamatsu Corp., Bridgewater, NJ) with a 20 µm pinhole.

Light that is generated in the sample by multi-photon processes has wavelengths different from (generally shorter than) that of incident beam 14. MPM signals collected by objective 25 are separated from the reflected beam 14 by a wavelength selective element 26 such as a dichroic mirror. The prototype embodiment used a dichroic mirror (FF665-Di02-25×36, Semrock, Inc.) for directing MPM signals into a detector for MPM signals.

Light arising from different multi-photon processes (e.g. SHG and TPF) can have different wavelengths and may be separated by a suitable wavelength selective element such as dichroic mirror. Additional filters may be provided to remove light other than the desired MPM signal(s).

In the FIG. 1 implementation, light deflected by wavelength selective element 26 is conditioned. For example the deflected light may be focused and/or short pass filtered. System 10 includes lens 27 and short pass filter 28. In the prototype embodiment short pass filter 28 was provided by (FF01-680/SP-25, Semrock, Inc.).

The conditioned light is split by wavelength selective element 29. In the prototype embodiment, element 29 is provided by a dichroic mirror (Di01-405-25×36 for 785 nm excitation, FF458-Di02-25×36 for 880 nm excitation Semrock, Inc). TPF signals are detected at a light detector 30A and SHG signals are detected at a light detector 30B. Light detectors 30A and 30B may, for example comprise photomultiplier tubes. In the prototype embodiment light detectors 30A and 30B were each provided by a model PMT, H9433MOD-03, photomultiplier tube from Hamamatsu Corp., Bridgewater, NJ.

Element 29 may be omitted in cases where it is unnecessary or not desired to separately collect TPF and SHG images. For example, SHG tends to be very low at 735 nm due to the low excitation efficiency for SHG at this wavelength. For imaging at 735 nm it can be desirable to leave element 29 as an empty space to allow the TPF and any SHG signal to be collected together by light detector 30A.

FIG. 1 shows additional filters 31A and 31B respectively before light detectors 30A, 30B. In the prototype embodiment filter 31B for SHG detection is provided by a band pass filter (FF01-390/40-25 for 785 nm excitation, FF01-440/40-25 for 880 nm excitation, Semrock, Inc.). In the prototype embodiment filter 31A for TPF detection is provided by a short pass filter (FF01-650/SP-25, Semrock, Inc.).

Signals output by light detectors 34, 30A and 30B which correspond to RCM, TPF and SHG signals are simultaneously collected. The signals may, for example, be collected by one or more frame grabbers. The prototype embodiment uses a Helios XA™, Matrox Electronic Systems Ltd., Canada to simultaneously sample all three signals. Because all three imaging channels use the same laser source 12, scanning unit 18 and z scanner 24, the three images are automatically co-registered.

The raw collected images are processed in an image processor 36 (which may comprise a programmed computer) and displayed on a display 38 and/or stored for later review and/or archival purposes.

Advantageously, scanning in the y-direction is performed by moving tissues relative to objective 25. When this is done, the length of the imaged tissue volume in the y-direction is not limited by objective 25 but can be much greater. For example, even with the best available objective lenses the maximum scan length achievable by scanning using scanning unit 18 is typically less than 1 mm (e.g. 200 µm in the prototype embodiment). By moving the tissue relative to the objective lens to scan in the y direction a much longer scan length may be achieved (e.g. several mm or 1 cm). This is advantageous because for some applications the typical dimensions of structures to be investigated exceed 1 mm. For example, early stage skin lesions that are possible candidates for melanoma or other diseases often have linear dimensions up to about 6 mm or more. In some embodiment, scanning in the y-dimension has a range of at least ±2 mm or ±5 mm. In some embodiments scanning in the y-direction has a range that is at least 2 or 4 or 5 times the maximum scanning range in the x direction.

It can be beneficial to provide a mechanism for stabilizing tissues being imaged. Such a mechanism may also be part of a mechanism that supports tissues to be imaged in a desired positional relationship to objective 25. A mechanism for y-axis scanning may incorporate a stage operable to move the stabilizing mechanism relative to objective 25. This movement may provide scanning in the y-direction.

A stabilizing mechanism may, for example comprise a stiff member (which may be called a "frame") that may be held in place on skin or other tissue adjacent to an area to be imaged. The frame may, for example, have the form of a ring that may be placed on skin or other tissue at a location such that the frame extends around a field of view of a desired imaging operation.

The frame surrounds a window opening through which tissue may be viewed. Depending on the application, the window opening may include a transparent coverslip which fills the window opening or a plate having an opening at a desired imaging location.

The frame is preferably detachably affixed to the structure that includes objective 25. This facilitates affixing the frame at a desired location on a patient. For example, if the patient has a mole or skin lesion that requires investigation the frame may be placed on the patient's skin such that the mole or other skin lesion lies within the window opening of the frame.

The part of apparatus 10 that includes objective 25 can then be brought to and coupled to the frame. For example, the frame may be magnetically attachable ton imaging head of apparatus 10.

The frame may be adapted to hold skin or other tissue in place. For example the frame may comprise a suitable adhesive which allows the frame to be removably adhered to skin or other tissue. The prototype embodiment included double sided tape to adhere a frame in the form of a ring to the skin of a patient.

Scanning unit 18, relay lenses 19, 20, z-scanner 24, objective 25 and light detectors 30A and 30B may be assembled together in a movable imaging head. Laser 12 and RCM light detector 34 may be provided in a separate unit. Light from laser 12 and the reflected RCM signal may be carried from and to the separate unit by way of a movable optical path such as an articulated mirror arm or suitable optical fibers. The imaging head may be positioned for skin imaging of different body sites of a living person or animal.

An adjustable stage or stages may be provided to help in aligning the imaging head to image a particular area.

FIG. 2 shows an example imaging head 50. Imaging head 50 includes a stage 51Z for adjustment of the position of objective 25 in a z direction. z stage 51Z may be used for real time position adjustment of the focal plane. Head 50 also includes stages 51X and 51Y for adjustment of the position of imaging head 50 in X and Y directions respectively relative to a tissue being imaged.

The prototype unit includes a z-translation stage (X-LSQ075A, Zaber Technologies) and motorized x- and y-translation stages (LNR25ZFS, Thorlabs). The xy translation stages are fixed on the base of the z stage. The x and y stages each have a range of motion of at least about ±2 mm. The y stage used in the prototype had a range of motion of 25 mm and is driven by a stepper motor and a 44:1 gear reduction head which provide a theoretical travel per microstep of 0.46 nm. An earlier prototype embodiment used a manually operated stage (CXY2 Thorlabs) that was modified to be driven by a stepper motor which provided 512 full steps per revolution. This provided a theoretical travel per full step of 0.5 µm and a moving resolution of 0.0625 µm.

The imaging unit together with the stages forms imaging head 50. Apparatus 10 may provide a support that allows Imaging head 50 to be easily moved to and supported at desired positions. For example, imaging head 50 may be supported by an articulated arm with counterweights.

FIG. 2 also shows an adaptor 53 that supports a detachable frame 54. Adaptor 53 is attached to x-stage 51X of imaging head 50. Adaptor 53 comprises a clear central through-hole. Magnets are spaced apart around adaptor 53. Frame 54 is received in a recess on the end of adaptor 53 and is held in place by the magnets. Frame 54 may be affixed onto skin using adhesive such as double-sided adhesive tape.

Figure 2A:
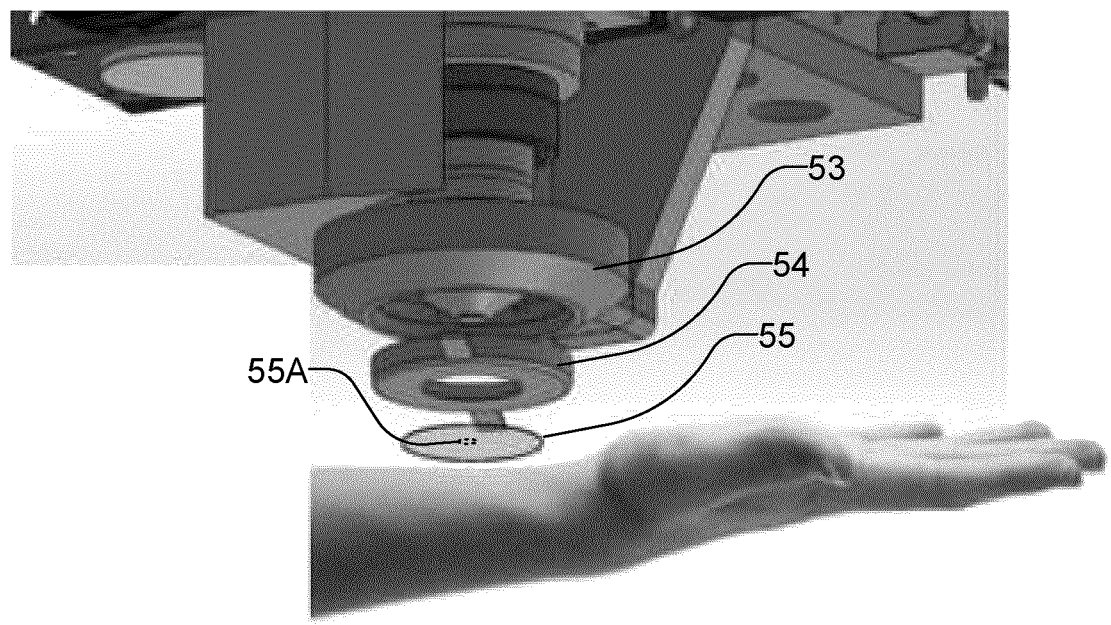
FIG. 2A is an exploded view of a skin-contacting portion of the imaging head of FIG. 2 including an adaptor and a detachable frame.

FIG. 2A is an exploded view showing adaptor 53, frame 54 and a plate 55 which optionally includes an aperture 55A for "direct measurement". For direct measurement, plate 55 may be a plastic plate. Aperture 55A may, for example comprise a hole having a diameter of about 5 mm. The plastic plate is attached to frame 54 and then frame 54 is attached to the skin site to be measured (e.g. by adhesive, for example, double sided tape on frame 54 and/or plate 55) with the measurement site located in the center of aperture 55A. Then frame 54 is mated into adapter 53 of the imaging head. Before measurement, drops of index matching fluid such as water are added between objective 25 and the exposed skin surface for refractive index matching.

An "indirect measurement" configuration may be used, for example when better motion suppression is necessary. In the indirect measurement configuration, plate 55 is an optically transparent plate such as a glass coverslip and the imaging is performed through plate 55. The coverslip is attached to frame 54 (e.g. by an adhesive such as double-sided tape). Then a drop of refractive index matching fluid such as water is added on the skin site to be measured. Then plate 55 is pressed onto the measurement site. A ring of adhesive such as ring-shape double-sided tape hold plate 55 onto the skin surface. Air bubbles between the coverslip and the skin surface should be avoided. Frame 54 may then be mated to adapter 53. Before measurement, drops of a refractive index matching fluid such as water are added between the objective and the coverslip for refractive index matching.

A controller is provided to coordinate the operation of the different parts of apparatus 10. The controller may, for example, comprise software executing on computer 36 which controls operation of scanner 18, z-scanner 24, y stage 51Y and frame grabber 35 by way of suitable interfaces and acquires data representing outputs of light detectors 30A, 30B and 34 by way of a suitable data acquisition system. For example, the entire prototype system is controlled by customized software written in C++ to control scanning, stage motion and data acquisition.

In some embodiments frame grabber 35 generates separate video streams for each of light detectors 30A, 30B and 34. Each of the video streams comprises a sequence of xz frame images.

Apparatus 10 can be operated to scan the point at which beam 14 is focused by objective 25 relative to tissue S to assemble an image point by point. Since the focus point can be scanned in all directions (x, y, z) by a combination of scanner 18, z-scanner 24, and stages 51X, 51Y and 51Z, apparatus 10 may be operated to obtain volumetric image information.

The xy translation stages 51X, 51Y can move the skin bidirectionally. In an example mode of operation, during volumetric imaging, the skin is moved only by the y stage while the focus point of beam 14 is scanned in x and z directions.

In some embodiments a direction in which skin or other tissue is moved relative to objective 25 is selectable without repositioning imaging head 50. For example, two stages such as stages 51X and 51Y may be operated in a coordinated fashion to move tissue relative to objective 25 in any direction in the xy plane. In such embodiments the direction scanned by scanning unit 18 is also adjustable to maintain the direction of scanning by scanning unit 18 transverse to the direction in which the skin or other tissue is moved. Rotation of the direction of scan by scanning unit 18 may be achieved by physically rotating scanning unit 18 and/or by providing a scanning unit 18 which includes two scanning mechanisms which are each operative to scan beam 14 and adjusting magnitudes and relative phases of driving signals for the two scanning mechanisms.

In a preferred mode of operation, scanning is performed in the xz plane (generally perpendicular to the surface of tissue S). A series of xz plane images that are spaced apart in the y direction are obtained. This series of images (which may be referred to as a sequence of "frames") may then be processed to yield a volumetric dataset. Preferably each xz plane image is acquired quickly enough that motion artifacts within an xz plane image are avoided or minimized. For example, each xz plane image may be acquired in about 100 ms or less.

Advantageously, scanning in the y direction is performed by operating y-stage 51Y. This stretches the tissue being imaged in the y direction. For example, volumetric data may be acquired by simultaneously scanning in the xz direction and (stretching) moving the skin with the translation stage in the y direction.

Apparatus 10 may incorporate a number of technologies that help to obtain high quality images. One of these technologies controls scanning in the x-z plane. Scanner 18 is generally faster than z-axis scanner 24 because scanner 18 does not move objective 25. As mentioned above, x-axis scanning may be performed by a fast scanner such as a resonant scanner. z-axis scanner 24 may be controlled in response to a synchronization signal that indicates when a scan has been completed in the x-axis direction.

In the prototype embodiment a varying DC voltage was used to drive a resonant scanner of scanner 18 to scan in the x direction. The maximum amplitude of the voltage determines the scanning range of the resonant scanner. Each time one line is scanned, the resonant scanner outputs a horizontal synchronization signal (Hsync). The control system provides control signals which ideally actuate scanner 24 (slow axis) to move one increment in the z direction for each Hsync period. To generate an image with a desired number M of rows at least M increments need to be executed in the z direction. For example, to generate an image having 512×512 pixels, at least 512 increments need to be executed in the z direction.

A problem is that because of mechanical effects such as inertia the position of slow axis (z-axis 24) may deviate from a position indicated by the drive signal for z-axis actuator 24. That is, a piezo positioner or other actuator which provides z-axis scanner 24 may not be able to completely follow the driving signal. If z-axis scanner 24 is driven by a sawtooth signal, the actual moving trajectory (z-position vs. time) will not be linear. This complicates image correction. When z-axis scanner 24 is driven by a sinusoidal signal, the actual moving trajectory are typically sinusoidal, but with phase shift and amplitude attenuation.

In some implementations the drive signal for z-axis scanner 24 is sinusoidal and is pre-compensated to compensate for such phase shifts and amplitude attenuation. This facilitates high-speed bidirectional imaging. In a prototype embodiment a piezoelectric z-axis scanner was used with a sinusoidal driving signal to operate at a scanning rate of 7.6 Hz (permitting a frame rate of 15 Hz when scanning bidirectionally).

Figure 4:
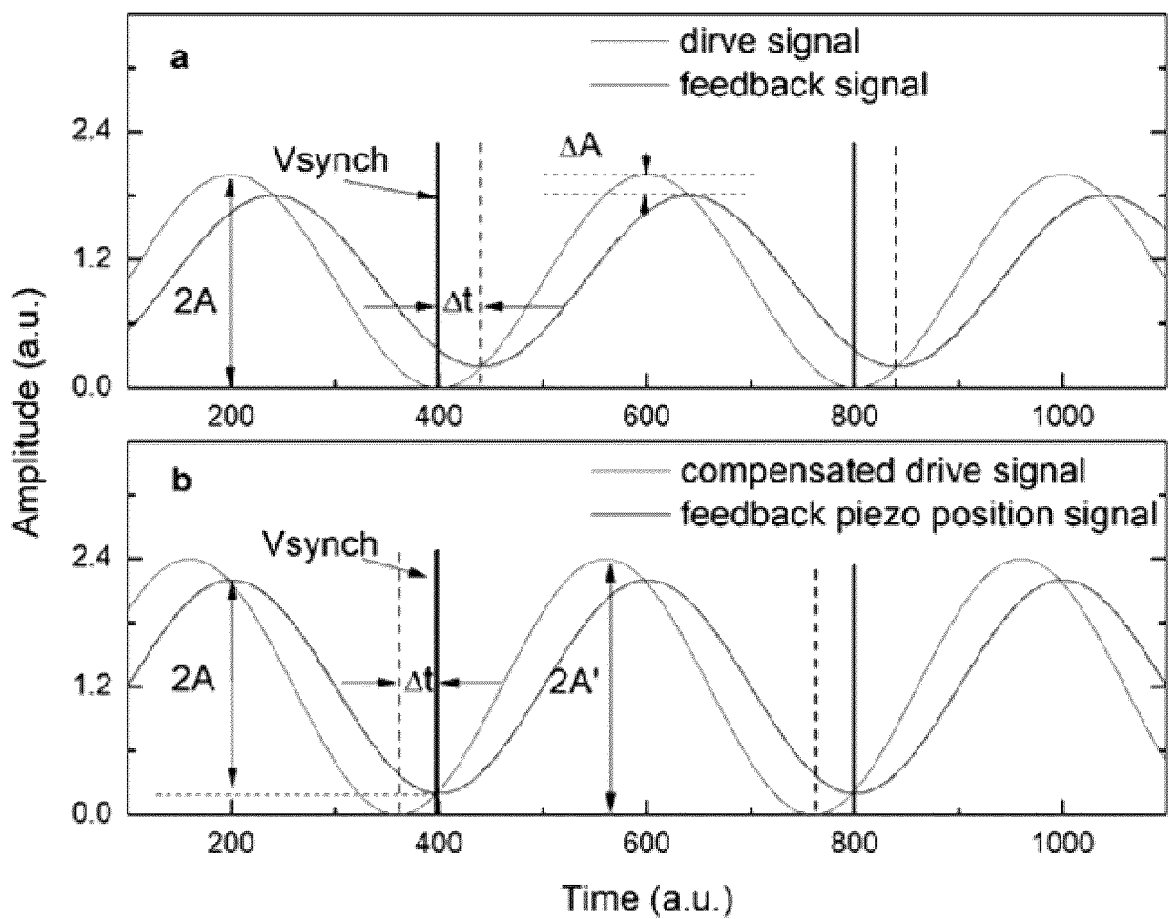
FIG. 4 illustrates a process for compensating for the phase shift and amplitude attenuation in a driving signal for z-axis scanning.

Compensation of the phase shift and amplitude attenuation may be accomplished based on monitoring the drive signal for z-axis scanner 24 and a position feedback signal from z-axis scanner 24. FIG. 4 illustrates the compensation process. The upper graph of FIG. 4 shows the time shift $\Delta t$ and the amplitude attenuation $\Delta A$ between the drive signal and the feedback signal. Time shift $\Delta t$ is the phase shift between the feedback signal and the vertical synchronization signal (Vsync) which marks the start of a new frame. The Vsync signal may, for example, be generated by a data acquisition interface after counting certain number of Hsync pulses. The number of Hsync pulses corresponding to one Vsync pulse may be equal to the number of lines that are scanned in a half scanning cycle for bidirectional imaging.

The drive signal for xz-scanner 24 may, for example, be given by:

$$y = A\cos\left(\frac{2\pi}{N}n\right) + A.$$

Here n refers to the ordinal of the line that is going to be scanned and N is the total number of lines that will be scanned in a full scanning cycle. The time period between adjacent lines equals to the time that the x-axis scanner takes to scan one single line ($T_R$). For the case where the x-axis scanner is an 8 kHz resonant scanner this time is ⅛₀₀₀ second. A is one half of the maximum amplitude of the drive signal.

For phase compensation, the original drive signal function was modified by adding a phase shift component $$\Delta n\left(\Delta n = \frac{\Delta t}{T_R}\right).$$

For amplitude compensation, A was replaced by A' to compensate for the attenuation. The compensated drive signal for xz-scanner 24 may, for example, be given by:

$$y = A'\sin\left(\frac{2\pi}{N}(n + \Delta n)\right) + A'.$$

After compensation, the actual motion of the piezo positioner matched the Vsync signal well and the amplitude of feedback signal had desired amplitude A as shown in the lower curve of FIG. 4.

Figure 3:
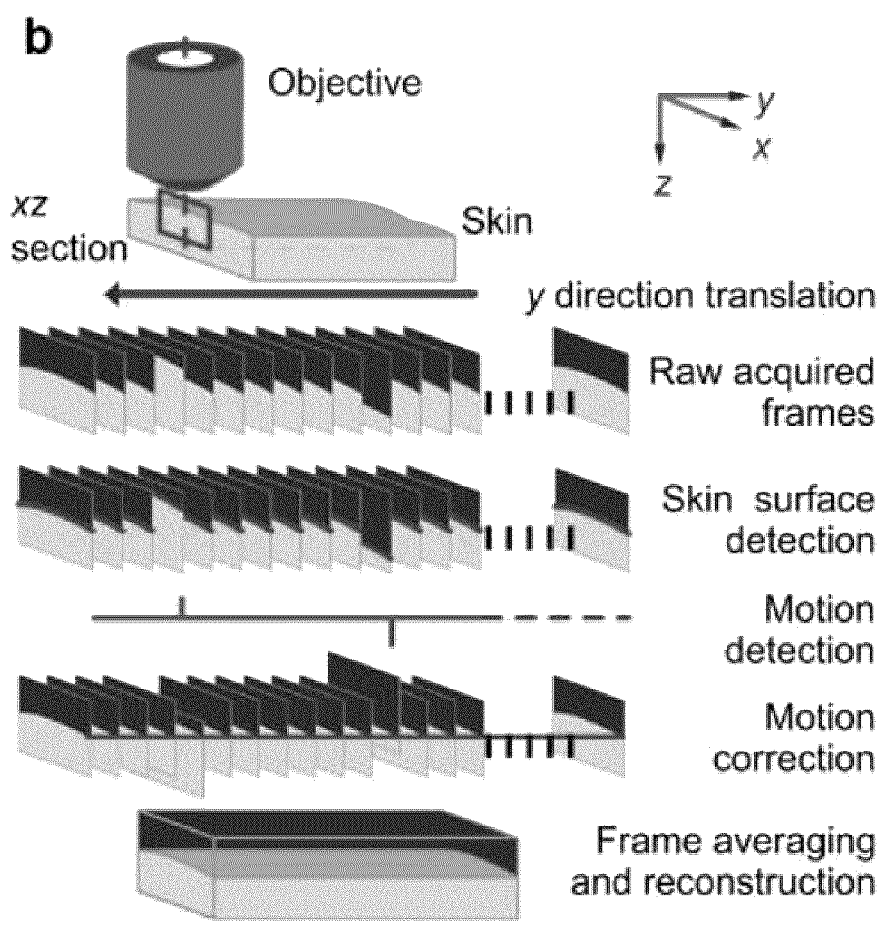
FIG. 3 illustrates a sequence of steps in an example process for generating volumetric image data from raw vertical plane image frames.

Another technique that helps to obtain high quality volumetric image data is bidirectional image acquisition. Bidirectional imaging makes full use of the scanning pattern of z-axis scanner 24 and speeds up imaging acquisition. One image is acquired as the z-axis is scanned in one direction (e.g. from shallower to deeper, downward as shown in FIG. 3) and a second image is acquired during scanning in the opposite direction (e.g. deeper to shallower, upward in FIG. 3). Bidirectional scanning allows frame rate to be doubled.

Figure 5:
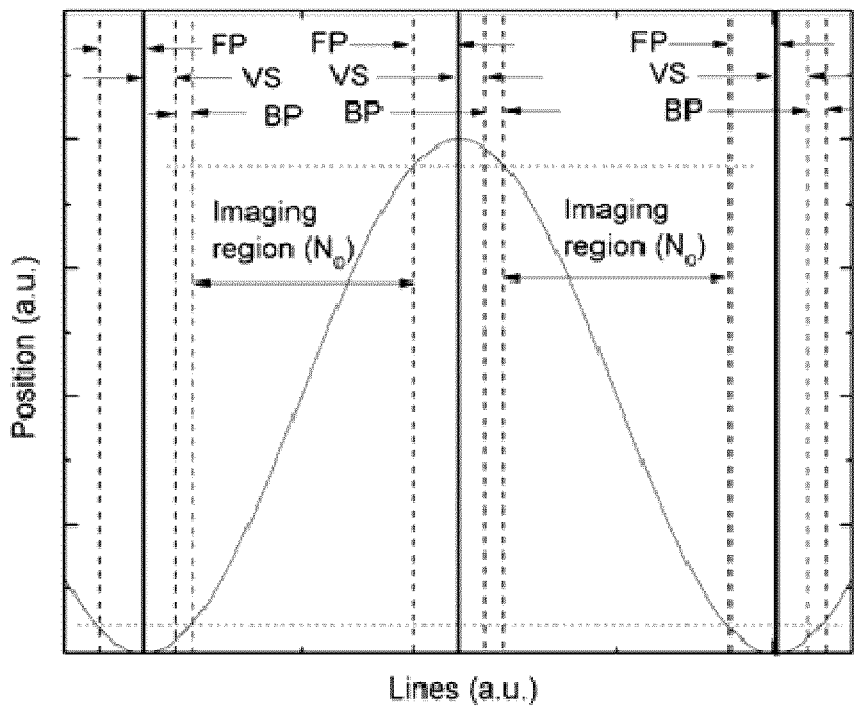
FIG. 5 illustrates video timing for bidirectional scanning.

Bidirectional imaging may be facilitated by generating a Vsync signal each time the z-axis scanning is reversed (i.e. one Vsync signal for each half-cycle of the drive signal for z-axis scanner 24. FIG. 5 illustrates video timing for bidirectional scanning.

For bidirectional imaging, an image acquisition device (e.g. frame grabber 35) is configured to acquire a separate image for each half-cycle of the z-axis drive signal. For example, a Digitizer Configuration File (DCF) may be used to configure frame grabber 35 to define video timing. Four parameters are set for vertical scanning: number of vertical lines per frame ($N_0$), Vertical Synchronization time (VS), Front Porch (FP) and Back Porch (BP).

The parameter VS sets time period for vertical synchronization. FP and BP respectively set time periods before and after VS when imaging is blanked. The time periods may be defined by numbers of horizontal scanning lines. The relationship of these parameters is shown in FIG. 5. Images are acquired between the end of BP and the start of the next FP.

For bidirectional imaging, it is necessary to keep the imaging zones of both the upward scanning and the downward scanning the same. Otherwise vertical scanning ranges in the two acquired images would likely be different. The DCF file may therefore set FP to be the same period of time as the sum of VS and BP. To make better use of the scanning area, FP can be made as short as possible and BP can be set to zero. In this way we can just keep FP having the same time period as VS. The total number of lines scanned in the z direction in a cycle is $N=2(N_0+VS+FP)$ where $N_0$ is the number of lines in the acquired image. In the prototype imaging system, $N_0$ is set to 512, VS=5 and FP=5, therefore totally N is 1044.

Bidirectional imaging does not need to be limited to the nearly linear region of the driving signal for z-axis scanner 24. Information from both upward and downward scanning is acquired. Therefore, almost the entire scanning cycle may be used.

FIG. 3 schematically illustrates the acquisition of a set of xz plane images and processing the set of xz plane images to obtain a high quality volumetric (3D) dataset. The processing includes: skin surface detection and adjustment, motion detection, motion correction and frame averaging. The volumetric imaging illustrated in FIG. 3 operates in the xz-y direction (i.e. obtaining xz frames that are closely spaced in the y direction) instead of the xy-z direction (i.e. obtaining xy frames that are closely spaced in the z direction.

Scanning in the y direction may be performed using a motorized translation stage (e.g. y-axis stage 51Y) to move the skin at a desired speed in the y direction while xz section images are continuously acquired as shown in FIG. 1A. An advantage of xz-y volumetric imaging is that the length of the scan in the y-direction can be arbitrarily long without requiring image stitching.

The spatial sampling rate in the y direction depends on the speed of scanning in the y direction. By making the y-scanning speed relatively small, one can compensate for low vertical resolution in scanned xz planes by obtaining scanned xz planes that are densely spaced in the y-direction and performing frame averaging to recover high SNR en-face images.

Frame averaging may be performed by selecting a scanning speed in the y-direction which will yield a desired number, N, of xz frames within a desired spatial resolution in the y-direction. For example, if a resolution of 1 μm is desired in the y-direction then the y-direction scanning speed may be set so that in the time taken for the tissue to be moved by 1 μm relative to objective 25 N xz frames are acquired. Where N=1 no averaging is performed. Where N≥2, the xz frames may be taken in groups of N frames, the pixel values for the N xz frames may then be pixelwise summed and the results of these operations divided by N to obtain an averaged xz frame. For example, if it is desired to obtain and average five xz frames for each 1 μm of scanning in the y-direction then the y-direction scanning speed may be controlled to cause a y-direction movement of 0.2 μm in the period taken to acquire one xz frame.

For example, images may be acquired using an imaging head 50 which is held in a fixed position as xz images are acquired. The skin may be moved in the y direction by y-axis stage 51Y. Anchoring of frame 54 and/or plate 55 to the skin surface by an adhesive (e.g. double sided tape) helps to reduce motion of the skin and helps to ensure that the skin is stretched and moved in the y direction as y-axis stage 51Y advances.

Another set of techniques that can helps to obtain high quality volumetric image data are techniques for correcting for distortions in the acquired images. These distortions These distortions can include:

With bidirectional imaging, images acquired while scanning in one direction are upside-down relative to images acquired while scanning in the other direction. In particular, images acquired during scanning from deeper to shallower are upside down compared to typical histological images in which the skin surface is upward.

Distortions due to non-linearity in scanning. For example, where a sinusoidal scanning pattern is used on either axis image data taken at equally spaced apart times do not correspond to locations that are equally spaced in the scanning direction especially at either end of the scan where the scanning pattern deviates most from being linear. A harder to address aspect of this kind of distortion is caused by hysteresis of the z-axis positioner. Hysteresis causes the actual trajectory of the z-axis scanner to depart from following an ideal sine wave. This can cause mismatch between the trajectories followed in opposed scanning directions. Because hysteresis caused distortion is nonlinear, it cannot be easily corrected by a standard sinusoidal algorithm as may be used for the resonance scanning in the x direction. A standard sinusoidal algorithm that may be applied to correcting positions of pixels in the x direction is described in reference [19].

All of these distortions may be corrected by redistributing each pixel of the raw image to a location corresponding to the actual location at which the pixel was obtained to construct a distortion-free image. This may be done using feedback position data from z-axis scanner 24.

Figure 6A:
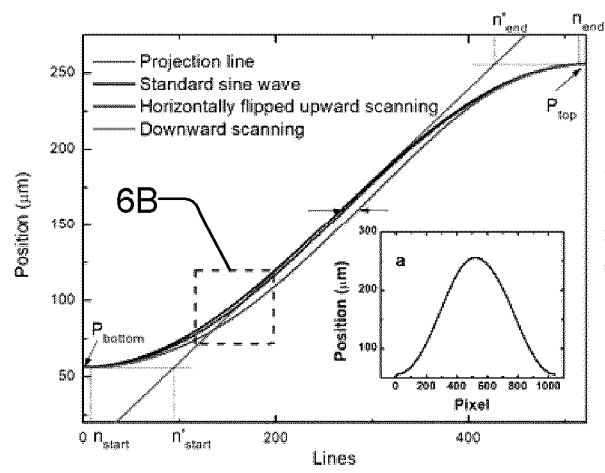
FIG. 6A is a graph which includes curves showing deviations in z-axis position from a driving signal for opposing scan directions.
Figure 6B:
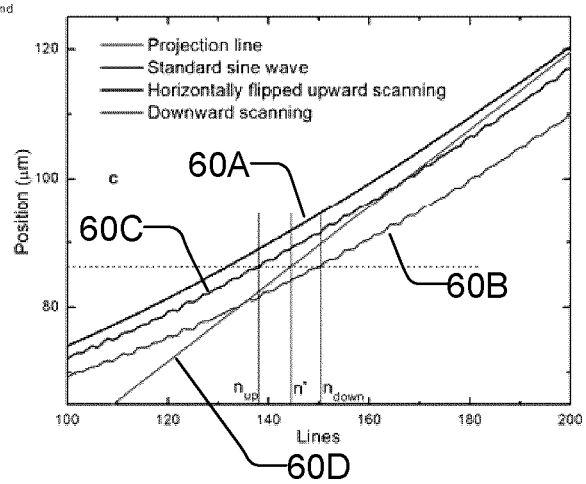
FIG. 6B is a blown up view of portion 6B of FIG. 6A.

FIGS. 6A and 6B illustrates the phenomenon of hysteresis during vertical scanning. FIG. 6B is an expanded view of portion 6B of FIG. 6A. In FIG. 6B, 60A is an ideal sinusoidal trajectory, 60B is an actual trajectory for scanning in the downward direction, 60C is an actual trajectory for scanning in the upward direction and 60D is a projection line that illustrates deviations of lines 60A, 60B and 60C from linearity. In FIGS. 6A and 6B lines 60B and 60C are feedback position data and position data of upward scanning line 60C is horizontally flipped for comparison to downward scanning line 60B.

A procedure for correcting the data is illustrated in FIG. 6B in which downward scanning (line 60B) is an example. Based on the first and last position data ($P_{bottom}$ and $P_{top}$) as well as the number of lines (N) scanned in each cycle, an ideal sinusoidal wave 60A is generated. This may be done using the following function:

$$F(n) = -A_0 \cos\left(\frac{2\pi}{N} n\right) + B_0$$

$$A_0 = \frac{P_{top} - P_{bottom}}{2};$$

$$B_0 = \frac{P_{top} + P_{bottom}}{2}.$$

Then a projection line 60D is generated which is tangent to the ideal sine wave at the middle point N/2. The slope of line 60D is $$K = \frac{2\pi A_0}{N},$$

and the line function is $L(n) = Kn + B_0 - \pi A_0$.

Downward scanning position curve 60B is named as DScan(n) and the flipped upward scanning position curve 60C as UScan(n). According to video timing, position data that corresponds to the acquired image can be determined. In this example, it is the $5^{th}$ to $516^{th}$ data points (index starts from 0). We name the start and end index as $n_{start}$ and $n_{end}$. These 512 position data are matched to the 512 pixel lines in the acquired raw image one by one. The position of each pixel lines in the raw image can be expressed as $P_{pixel\_index} = \text{DScan}(\text{pixel\_index} + n_{start})$. The pixel index also starts from 0. The next step is to determine the number of pixel lines for the corrected image. Both DScan($n_{start}$) and DScan($n_{end}$) are projected to the horizontal axis through projection line L to get the new start and end index ($n'_{start}$ and $n'_{end}$) for the corrected image. The number of pixel lines for the corrected images are therefore $n'_{end} - n'_{start} + 1$. And the position of each pixel line in the corrected image can be calculated as $P_{pixel\_index'} + L(\text{pixel\_index'} + n'_{start})$.

For each $P_{pixel\_index'}$, $L(n' = \text{pixel\_index'} + n'_{start})$ is compared to all the position data inside on DScan curve to find the nearest one (say $n_{down}$). A match relation between all n' and $n_{down}$ is then built and expressed as an array: $M(n') = n_{down}$ (n' starts from $n'_{start}$ to $n'_{end}$).

Finally, each pixel line of the corrected image will find and be replaced by a corresponding pixel line in the raw image using the actual position as an intermediate parameter:

$$P_{pixel_{index'}} = L(pixel_{index'} + (n'_{start})) =$$

$$DScan(M(pixel_{index'} + n'_{start})) = P_{M(pixel\_index' + n'_{start}) - n_{start}}.$$

Therefore, a pixel line with the index of pixel_index' in the corrected image will be replaced by a pixel line with the index of M(pixel_index'+$n'_{start}$)-$n_{start}$ in the raw image.

Similar to the standard sinusoidal algorithm, the above correction method will also lead to decreased pixel number in the vertical direction, especially in the top and bottom regions. The vertical line number of the corrected image, in this case, decreased to 337 from the original number 512. The new image was expanded to 512 lines through linear interpolation. Finally, the image was binned by a factor of 2 along both x and z direction to increase the signal to noise ratio.

The same correction method may be performed for the upward scanning image. Since each pixel in the corrected image was placed according to its actual position, all three kinds of distortions mentioned above can be corrected at the same time.

In many applications the motion of a z-axis scanner such as a piezo positioner will be consistent from one scan to another. In such applications it is unnecessary to acquire z-axis position feedback data for every scanning cycle. Position feedback data (e.g. data indicating actual z position of the z-axis scanner as a function of time during a full scan cycle) may be acquired once or periodically. For example, position feedback data may be acquired once at a time after motion of the z-axis scanner has stabilized (e.g. at the tenth scanning cycle). Position feedback data may be acquired each time a new imaging operation starts. The position feedback data may be stored and used for distortion correction as described, for example, above.

Acquired image data may be processed by a motion correction algorithm. Where the tissue being imaged is skin, the motion correction algorithm may apply the fact that skin surface is continuous. The motion during imaging is firstly detected and then the volumetric data is motion corrected accordingly. FIG. illustrates a motion detection procedure.

For each frame the skin surface position is determined. This may be done by detecting a step in image intensity that corresponds to the skin surface. For example, each frame of raw RCM data may cover a z-axis depth range which spans from index matching fluid, through the skin surface to deeper tissue layers. The index matching fluid typically scatters little light and shows up as a dark region. The interface between the index matching fluid and the skin surface typically scatters a lot of light and is bright in the RCM images.

A frame imaging an x-z plane may be processed by, performing intensity thresholding starting at the top. This may be performed for each column. The surface may be identified, for example, as the first pixel in the column having a pixel value exceeding a threshold or the first of a group of N consecutive pixels in the column having pixel values exceeding the threshold (with N=2 for example).

Figure 7B:
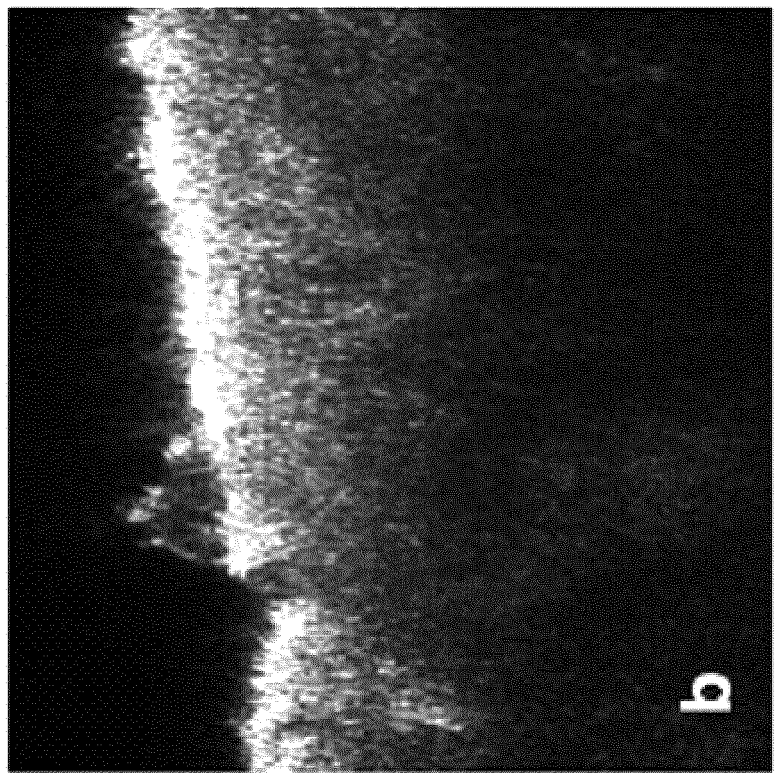
FIGS. 7A to 7F illustrate a motion correction between two adjacent frames.
Figure 7A:
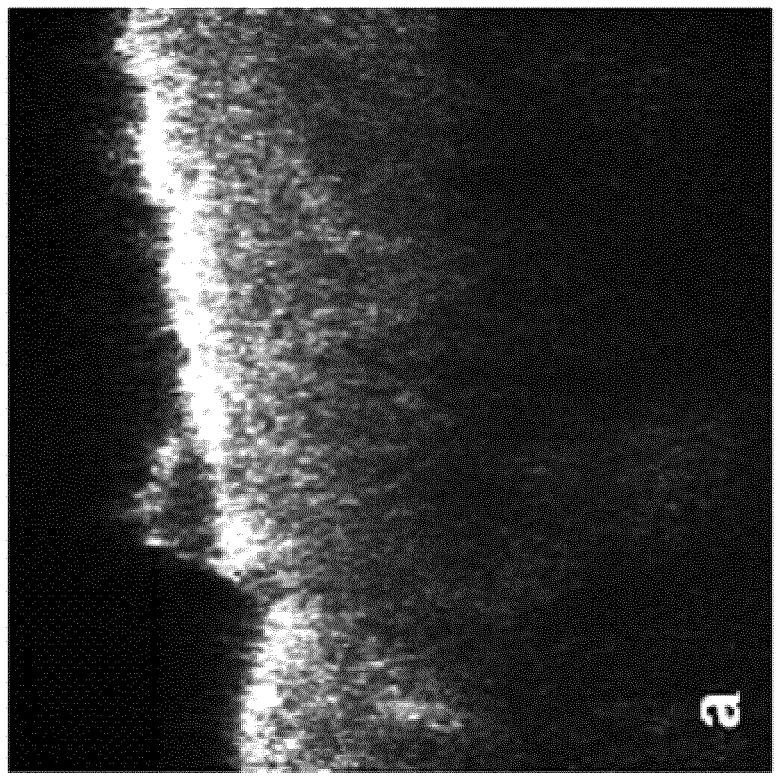
Figure 7D:
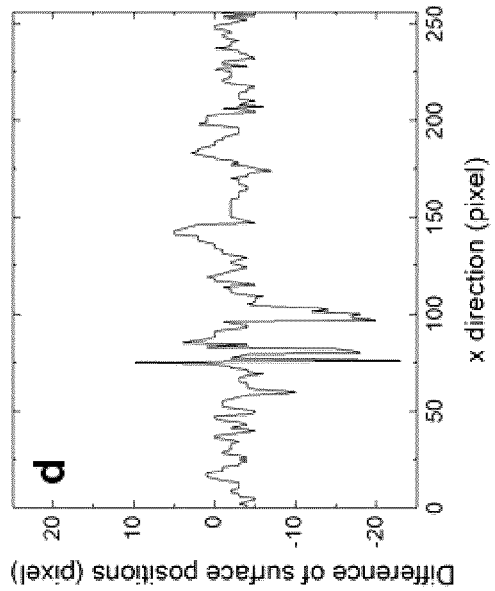

The threshold may, for example be selected to have a high enough value that all or nearly all pixels corresponding to locations in the index matching fluid have values below the threshold while all or nearly all pixels corresponding to locations at the skin surface have values above the threshold. For example, the threshold may be selected to be in a range of 15% to 55% of a maximum pixel value. For the case where pixel values are 8 bit values (values in the range of 0 to 255) the threshold may be in the range of about 40 to 140 for example. Where this is done for each column in the image the result is an array, $S_n$, of values representing the row index corresponding to the skin surface. The subscript n is the numeric index of the frame. Two adjacent frames are shown in FIGS. 7(a) and 7(b) and their detected surface arrays are plotted in FIG. 7(c).

Motion between frames can be detected and quantified by comparing the skin surface positions in different frames. This may be done, for example, by computing a difference-array (Diff$_n$) by subtracting corresponding indices representing the skin surface in two neighboring frames (i.e. by calculating Diff$_n$=S$_n$-S$_{n-1}$).

Figure 7E:
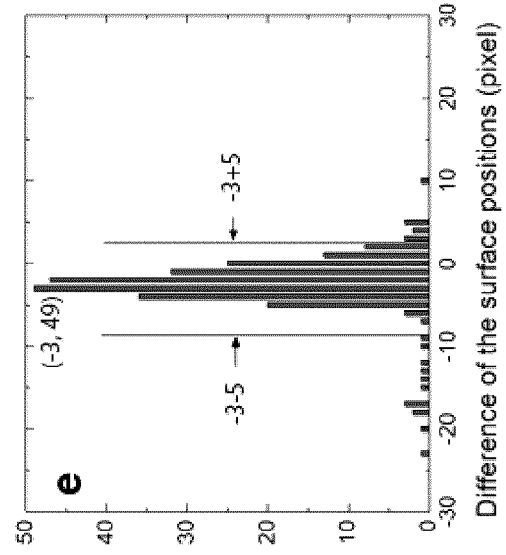
Figure 7C:
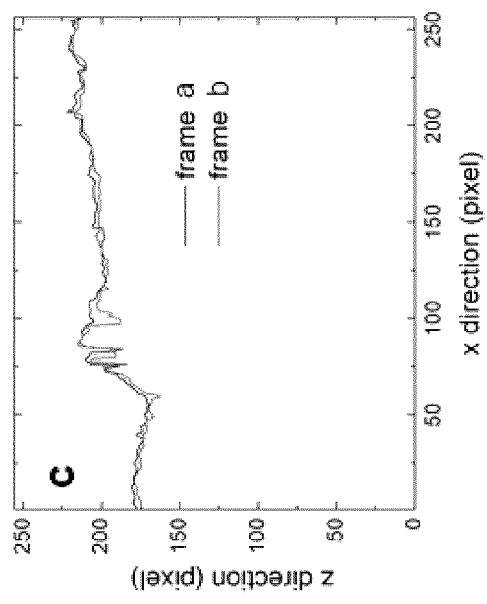

Preferably Diff$_n$ is processed to eliminate 'outliers' (i.e. values in Diff$_n$ that depart form a value that is representative of all of the values in Diff$_n$ by more than a given amount). The representative value may, for example be the mode, $d_{mode}$, which is the most frequently appearing value within Diff$_n$. FIG. 7E is an example frequency histogram of Diff$_n$ for two example frames. FIG. 7E shows the number of occurrences for each difference-value. The most frequently appearing value d$_{mode}$ within Diff$_n$ is the value with the greatest frequency. Outliers may be eliminated by eliminating values in Diff$_n$ that are outside of a selection window centered on d$_{mode}$. For example, the selection window may be from d$_{mode}$-5 to d$_{mode}$+5. Any element of Diff$_n$ with its value not sitting within the window may be deleted or ignored or replaced by d$_{mode}$.

Figure 7F:
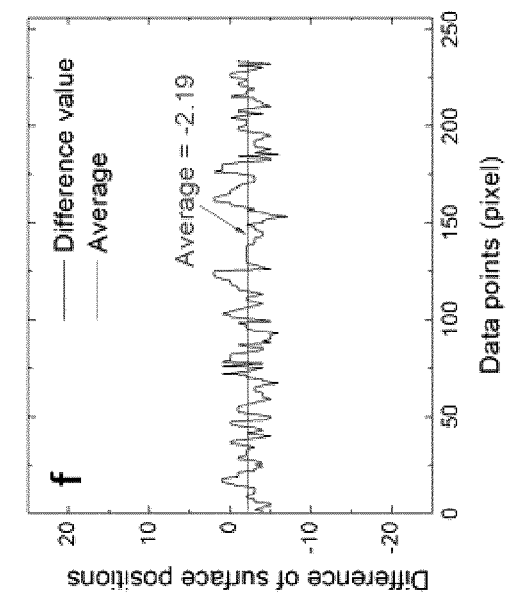

After outliers are eliminated the difference array may be called Diff'$_n$. An example is illustrated in FIG. 7D. In that example the values with the most counts have differences between −8 and 5. d$_{mode}$ is −3 which has a count of 49. FIG. 7F is a plot of the example Diff'$_n$ with 22 outlier data points having been filtered out.

Relative motion between two frames can be estimated using a representative value (e.g. the average value) of Diff'$_n$. In the example of FIG. 7F, the average value of all the data points is −2.19, which is treated as indicating the relative motion between the two frames (in this case the frames shown in FIGS. 7A and 7B.

To retain the surface profile of the volume, differences Diff'$_n$ with average values smaller than 0.5 pixels may be re-assigned as zero, thus assuming no motion.

The above method may be applied to determine the relative motions of all frames (e.g. by comparing each frame after the first frame to the previous frame). One example way to determine relative motions of all of the frames is to generate a motion curve (the black line) as shown in FIG. 8A. The motion curve shows every frame's total motion relative to the first frame by adding up all the previous relative motions.

According to the motion curve, every frame may be shifted vertically by the determined number of pixels to remove the motion.

For practical reasons, it can be desirable to offset the motion curve by its linear regression fitting line. This is illustrated in FIGS. 8A to 8D. FIG. 8A shows a motion curve, a linear regression fitting line and an adjusted motion curve. FIG. 8B illustrates a 3D motion corrected volumetric image. FIG. 3C shows one vertical plane image of the motion corrected volume. FIG. 3D shows the vertical plane image of FIG. 8C before motion correction. In FIGS. 8B to 8D the scale bar has a length corresponding to 200 µm.

A straight line 62A is fit to original motion curve 62B. For each data point in the original motion curve, the corresponding value in the linear regression fitting line 62A is subtracted from the value in motion curve 62B to yield a realigned motion curve 62C. Curve 62C has an overall flat trend.

FIGS. 8B and 8C illustrate motion corrected results. FIG. 8B is an example reconstructed 3D volume image. A continuous skin surface is recovered without being oversmoothed. FIG. 8D shows the corresponding yz plane image of the raw volume (without motion correction). By comparing FIGS. 8C and 8D one can see that the described method retains skin surface information. The white arrow and black arrow point to protruding structures on the skin surface which are well kept after motion correction. The frameshifting procedure leaves a trace as highlighted by the dotted line in FIG. 8C.

Optionally the volumetric image may be processed to flatten the skin surface. Since the skin surface is generally not flat but has furrows, different points on an x-y plane in the volumetric image data can correspond to different depths below the skin surface. As a result, different skin layers are often sectioned in a single x-y plane. Although frequently used for comparison studies, such sections are not convenient for comparing cellular or tissue structures at the same tissue depth especially in a large field of view. To address this problem one can apply a surface-flatting method to make the overall skin surface of the volume lie in one plane.

Surface flatting may be performed as follows. A skin surface profile for the motion-corrected volumetric image may be obtained. The skin surface profile may, for example, comprise a 2D array whose values specify a location (e.g. z-axis position or pixel index) of the skin surface at each x-y location. This skin surface profile may be called S_volume. One way to generate S-volume is to shift each S$_n$ by the corresponding motion adjustment (e.g. as determined from the motion curve as described above) and to populate each row of S_volume with a corresponding one of the adjusted S$_n$.

The skin surface profile S_volume may then be spatially filtered to obtain a low spatial frequency profile of S_volume. The low spatial frequency profile of S_volume shows the overall curvature of the skin surface without reference to highly localized features.

2D low pass spatial filtering may, for example comprise symmetrically padding S_volume In order to avoid edge effects. In a prototype implementation S_volume was padded all around by 200 pixels. In this prototype implementation, S_volume initially had a dimension of 256 by 4071 pixels. After padding the padded version of S_volume had dimensions of 656 by 4471 pixels.

Low-pass filtering may comprise performing a Fourier transform (e.g. a discrete Fourier transform–DFT) of the padded version of S_volume. In a DFT, the frequency domain image has the same dimension as the raw image. However the interval at which the DFT is sampled is the reciprocal of the dimension of the input. Therefore, the same 2π spatial frequency has different samples in the x and y directions.

The Fourier transformed image may then be filtered to remove high spatial frequency components. Filtering may comprise multiplying the Fourier domain data by a filter function. For example, a prototype embodiment used a first order 2D Butterworth filter with the function:

$$H_{butterworth} = \frac{1}{1 + \left(\frac{x-x0}{dx}\right)^2 + \left(\frac{y-y0}{dy}\right)^2}$$

Where x and y are coordinates of points in the Fourier domain image, x0 and y0 are the coordinates of the center of the image and dx and dy correspond to the cutoff spatial frequency in the x and y directions. In the prototype the cut-off frequency was set at 2π/25, which means the two ratios dx to dimension in x direction and dy to the dimension in y direction were set at ¹⁄₂₅.

After filtering, an inverse discrete Fourier transform may be applied to yield low pass filtered 2D padded surface data. The padding may then be deleted. The low pass filtered 2D padded surface data may then be used to determine how far each (z-direction) column in the volumetric image data should be shifted so that the skin surface in each column is aligned at a desired horizontal (x-y) plane. For example, an xy plane that passes through a maximum of the low pass filtered 2D padded surface data or a maximum of the skin surface profile in the first frame may be chosen. Once the xy plane is chosen, the z-direction distance Sdiff$_{toflat}$ between the low pass filtered 2D padded surface data and the xy plane is calculated for each column in the volumetric data. Each column can then be shifted by the amount corresponding to the column in $\text{Sdiff}_{toflat}$ to obtain flattened data.

Since motion correction and flattening can each involve shifting columns in the volumetric data up or down one can optionally combine the shifts for motion correction and surface flatting and apply the combined shifts together. In this case, the correction array $A_{correction}$ may be calculated by adding the corresponding values of the motion curve array as discussed above to the $\text{Sdiff}_{toflat}$, and then shifting every column of the raw volume data according to the corresponding value of $A_{correction}$.

Since data for plural imaging modalities (e.g. RCM, TPF and SHG) are co-registered pixel shifts determined for one imaging mode may be applied to other co-registered imaging modes also. For example, pixel shifts determined with reference to the RCM images may be applied to TPF, SHG or other images also. This can be particularly useful in a case where one imaging modality is relatively 'sparse' such that it may be difficult to identify the skin surface or to accurately determine the effects of motion for that imaging modality.

As described above, the methods and apparatus described herein may be applied to obtain 3D image data for a volume that has a large extent in one direction (y-direction). The methods and apparatus may be applied to obtain 3D image data that is larger in two dimensions than could be achieved by scanning beam 14 alone by repeating the described methods for overlapping volumes. For example, plural sets of image data may be obtained as described above but with stage 51X adjusted to provide x-direction offsets between the volumes imaged by the different sets of 3D image data. The offsets may be chosen so that the volumes overlap somewhat Image stitching techniques may be applied to create a mosaic which is extended in both x- and y directions.

While the techniques described herein may be applied to imaging skin, they may also be applied to image other body tissues. For example the described methods may be applied intraoperatively. Where tissues other than skin are being imaged a tissue surface or other body surface may be used in place of the skin surface for motion compensation and/or flatting.

In some applications it can be desirable to create a temporary or permanent record of where on a subject's anatomy a particular volume was imaged. In some embodiments apparatus as described herein may be applied to mark a location of an imaging operation. This may be done for example by controlling beam 14 to heat a small section of tissue sufficiently to bleach burn or otherwise alter the appearance of the tissue to leave indicia indicating the site at which one or more sets of image data was acquired. Apparatus as described herein may include other indicia marking devices for example, pens, ink jet markers, or the like.

Example 1

Fast speed vertical section imaging was tested on dorsal forearm skin of a 46-year-old Asian male volunteer using an excitation wavelength of 785 nm and laser power of 50 mw. Information from all three channels (RCM, SHG and TPF) was combined In a pseudo-color image which showed multiple skin layers.

The RCM image showed a distinct three-layer structure running parallel to the skin surface. The structure included one dark layer sandwiched between two bright layers. The uppermost bright layer is presumed to represent the stratum corneum which is the most superficial epidermal layer. This layer is made of terminally differentiated, non-viable cells containing keratin. With strong signals from both RCM and TPF channels, this layer appears magenta in the pseudo-color RGB image. The second bright layer in the RCM image was assumed to be the stratum granulosum which should have high reflectance due to the presence of dense keratohyaline granules. The middle dark layer in the RCM image which appears empty contains fluorescence-rich materials (appearing as a blue band) and is assumed to be a more compacted lower part of stratum corneum.

Stratum basale was seen as a band filled with bright spots in both the RCM and TPF images. These bright signals are from melanin-rich keratinocytes. Under the stratum basal, distinctive signals in the SHG channel showed collagen distribution within dermal papillae.

With vertical-section multimodal imaging the location of the dermal-epidermal junction is more obviously apparent than with any single channel. The ability to identify this boundary is important because most skin cancers start from this region. Moreover, visualizing the skin surface and dermal-epidermal junction allows the epidermis to be delineated more clearly in terms of shape and thickness as compared to previously reported methods.

The imaging speed of the prototype system (about 15 fps) was found to be sufficient to observe dynamic capillary blood flow within the dermal papilla in the vertical plane.

Example 2

Fast vertical plane imaging as described herein allows large field volumetric optical biopsy. To demonstrate this capability a 200 µm×200 µm×3.2 mm volumetric optical biopsy on normal forearm skin was acquired from the forearm of a volunteer with co-registered RCM, SHG and TPF channels. The raw data had the form of three videos each made up of 4072 frames. Each frame was an xz plane image having a resolution of 256 pixels by 256 pixels. In this example, the averaging factor was 1 (i.e. the y scanning speed was selected so that the spacing in the y direction between adjacent frames was equal to a desired resolution in the y direction). The whole volume was acquired in 4.5 minutes. The excitation wavelength was 880 nm at a laser power of 40 mw.

At a wavelength of 880 nm, epidermal cells have low excitation efficiency while collagen generates better SHG signals. The RCM, TPF and SHG channels were merged to obtain multi-contrast wide field volumetric optical biopsy data. Motion correction was applied as described above and was found to greatly reduce the effect of minor and major motion-caused vibrations while retaining skin surface texture including hair, skin flakes, other debris and surface roughness.

The SHG channel showed a 3D collagen distribution. SHG and TPF channels combined outlined the stratum corneum and dermis. The SHG channel combined with both TPF and RCM channels clearly outlined the epidermis to dermis junction in yz plane images over a wide field. xy plane images at a selected z depth showed epidermal cellular and tissue information together with a high resolution RCM image.

Since the skin surface was not flat but had furrows, different skin layers were sectioned in a single xy plane. The data was then processed for surface flatting as described above. This resulted in images of normal skin tissue in which tissue structures are similar at the same tissue depth.

In the volumetric data it was possible to view skin appendages like sweat glands and hair follicles three dimensionally.

Example 3

An excitation wavelength of 735 nm was used to acquire volumetric optical biopsy data with high TPF cellular resolution. A 200 µm×200 µm×2.5 mm volume on normal forearm skin was acquired from a volunteer with both RCM and TPF channels made up of 15000 frames and a resolution of 256 pixels by 256 pixels. The laser power was 40 mw. The averaging factor is 5. The whole volume was acquired in 17 minutes. The SHG signal was not separated from the TPF channel because of the low excitation efficiency of collagen at 735 nm.

With TPF contrast, high resolution cellular morphology changes from large polygon keratinocytes in stratum corneum to small and bright basal cells were observed. It was also possible to locate any cell's 3D spatial position.

Surface-flatting was applied to the volumetric data to make it easier to compare cellular morphology in a large field of view at the same tissue depth.

With the mapping of RCM to green, TPF to red, SDH to yellow at an excitation wavelength of 735 nm, most epidermal cells appear as having green borders, red content and dark centers. This can be explained by the high reflectance of cell-cell junctions, high TPF signals of NADH in the cell cytoplasm and weak signals of the cell nucleus. Some cells have a green center which arises from reflectance of a cell nucleolus. Although merging the RCM and TPF channels gives some complementary information, it can be better to view the cell morphology in the TPF channel alone to avoid the effect of RCM image which has a relatively lower resolution. The horizontal (xy) plane TPF image of the skin surface shows bright patches sparsely distributed in the whole field of view. High-resolution cell morphology is clearly visualized at a depth of 19 µm and 28 µm.

The wide field volumetric data acquisition time depends on the translation speed and translation length in the y direction. Slower speeds lead to higher frame averaging factors and thus higher SNR but longer acquisition times. The acquisition time of Example 2 and Example 3 were respectively 4.5 minutes with an averaging factor of 1 and 17 minutes with an averaging factor of 5.

A benefit of the larger averaging factor and longer acquisition time in Example 3 is that an acceptable SNR can be achieved despite the weak excitation efficiency of label free TPF. In comparison, RCM signals are generally strong enough for a good image without averaging. Averaging is typically not needed in the SHG channel if it is only the overall distribution of SHG that is of interest.

The foregoing examples demonstrated, among other things, that motion correction as described herein applied to vertical plane images can detect and correct the effects of motion whether the acquisition time is long or short as long as the motion amplitude is within the field of view. Image acquisition speed may be selected based on the application.

These examples demonstrate that fast xz sectioning based xz-y multimodality volumetric skin biopsy can address the most common challenges during in vivo imaging including involuntary movement, low SNR, limited contrast, small field of view and loss of 3D spatial information. Furthermore, and surprisingly the described methods are capable of generating subcellular resolution morphology images in the horizontal plane by processing the acquired 3D volumetric data.

Interpretation of Terms

Unless the context clearly requires otherwise, throughout the description and the claims:

"comprise", "comprising", and the like are to be construed in an inclusive sense, as opposed to an exclusive or exhaustive sense; that is to say, in the sense of "including, but not limited to";

"connected", "coupled", or any variant thereof, means any connection or coupling, either direct or indirect, between two or more elements; the coupling or connection between the elements can be physical, logical, or a combination thereof;

"herein", "above", "below", and words of similar import, when used to describe this specification, shall refer to this specification as a whole, and not to any particular portions of this specification;

"or", in reference to a list of two or more items, covers all of the following interpretations of the word: any of the items in the list, all of the items in the list, and any combination of the items in the list;

the singular forms "a", "an", and "the" also include the meaning of any appropriate plural forms.

Words that indicate directions such as "vertical", "transverse", "horizontal", "upward", "downward", "forward", "backward", "inward", "outward", "left", "right", "front", "back", "top", "bottom", "below", "above", "under", and the like, used in this description and any accompanying claims depend on the orientation of the apparatus and/or tissues as described and illustrated. The subject matter described herein may assume various alternative orientations. Accordingly, these directional terms are not strictly defined and should not be interpreted narrowly.

Embodiments of the invention may be implemented using specifically designed hardware, configurable hardware, programmable data processors configured by the provision of software (which may optionally comprise "firmware") capable of executing on the data processors, special purpose computers or data processors that are specifically programmed, configured, or constructed to perform one or more steps in a method as explained in detail herein and/or combinations of two or more of these. Examples of specifically designed hardware are: logic circuits, application-specific integrated circuits ("ASICs"), large scale integrated circuits ("LSIs"), very large scale integrated circuits ("VLSIs"), and the like. Examples of configurable hardware are: one or more programmable logic devices such as programmable array logic ("PALs"), programmable logic arrays ("PLAs"), and field programmable gate arrays ("FPGAs"). Examples of programmable data processors are: microprocessors, digital signal processors ("DSPs"), embedded processors, graphics processors, math co-processors, general purpose computers, server computers, cloud computers, mainframe computers, computer workstations, and the like. For example, one or more data processors in a control circuit for an imaging device may implement methods as described herein by executing software instructions in a program memory accessible to the processors.

Processing may be centralized or distributed. Where processing is distributed, information including software and/or data may be kept centrally or distributed. Such information may be exchanged between different functional units by way of a communications network, such as a Local Area Network (LAN), Wide Area Network (WAN), or the Internet, wired or wireless data links, electromagnetic signals, or other data communication channel.

While processes or blocks are presented in a given order, alternative examples may perform routines having steps, or employ systems having blocks, in a different order, and some processes or blocks may be deleted, moved, added, subdivided, combined, and/or modified to provide alternative or subcombinations. While elements are at times shown as being performed sequentially, they may instead be performed simultaneously or in different sequences. Each of these processes or blocks may be implemented in a variety of different ways.

The invention may also be provided in the form of a program product. The program product may comprise any non-transitory medium which carries a set of computer-readable instructions which, when executed by a data processor, cause the data processor to execute a method of the invention. Program products according to the invention may be in any of a wide variety of forms. The program product may comprise, for example, non-transitory media such as magnetic data storage media including floppy diskettes, hard disk drives, optical data storage media including CD ROMs, DVDs, electronic data storage media including ROMs, flash RAM, EPROMs, hardwired or preprogrammed chips (e.g., EEPROM semiconductor chips), nanotechnology memory, or the like. The computer-readable signals on the program product may optionally be compressed or encrypted.

Where a component (e.g. a software module, processor, assembly, device, circuit, etc.) is referred to above, unless otherwise indicated, reference to that component (including a reference to a "means") should be interpreted as including as equivalents of that component any component which performs the function of the described component (i.e., that is functionally equivalent), including components which are not structurally equivalent to the disclosed structure which performs the function in the illustrated exemplary embodiments of the invention.

Specific examples of systems, methods and apparatus have been described herein for purposes of illustration. These are only examples. The technology provided herein can be applied to systems other than the example systems described above. Many alterations, modifications, additions, omissions, and permutations are possible within the practice of this invention. This invention includes variations on described embodiments that would be apparent to the skilled addressee, including variations obtained by: replacing features, elements and/or acts with equivalent features, elements and/or acts; mixing and matching of features, elements and/or acts from different embodiments; combining features, elements and/or acts from embodiments as described herein with features, elements and/or acts of other technology; and/or omitting combining features, elements and/or acts from described embodiments.

Various features are described herein as being present in "some embodiments" or "in some implementations". Such features are not mandatory and may not be present in all embodiments or implementations. Embodiments and implementations of the invention may include zero, any one or any combination of two or more of such features. This is limited only to the extent that certain ones of such features are incompatible with other ones of such features in the sense that it would be impossible for a person of ordinary skill in the art to construct a practical embodiment or implementation that combines such incompatible features. Consequently, the description that "some embodiments" or "some implementations" possess feature A and "some embodiments" or "some implementations" possess feature B should be interpreted as an express indication that the inventors also contemplate embodiments and implementations which combine features A and B (unless the description states otherwise or features A and B are fundamentally incompatible).

It is therefore intended that the following appended claims and claims hereafter introduced are interpreted to include all such modifications, permutations, additions, omissions, and sub-combinations as may reasonably be inferred. The scope of the claims should not be limited by the preferred embodiments set forth in the examples, but should be given the broadest interpretation consistent with the description as a whole.

What is claimed is:

1. A method for imaging tissue, the method comprising:
   focusing a beam of light to a focus point;
   raster scanning the location of the focus point across a field of view in a vertical plane extending generally perpendicular to a surface of the tissue and collecting and detecting light returning from the focus point to provide a first xz plane image;
   scanning the location of the focus point in a y-direction transverse to the vertical plane to obtain a sequence of additional xz plane images corresponding to vertical planes parallel to and spaced apart in a y-direction from the vertical plane, the first xz plane image and the additional xz plane images constituting a set of xz plane images; and
   processing the set of xz plane images to provide volumetric image data for the tissue;
   wherein scanning the location of the focus point in the y direction comprises holding the objective fixed in the y direction while moving the tissue in the y direction.

2. The method according to claim 1 wherein focusing the beam of light comprises passing the light through an objective and raster scanning the location of the focus point comprises optically scanning the beam in an x direction in coordination with scanning the objective relative to the tissue along a z axis which is generally perpendicular to the x direction and to the surface of the tissue.

3. The method according to claim 1 wherein moving the tissue in the y direction comprises operating a linear motion stage coupled between the objective and a member adhered to a surface of the tissue.

4. The method according to claim 1 wherein a range of the scanning in the y direction is at least three times larger than a range of the scanning in the x direction.

5. The method according to claim 1 comprising separating and detecting a plurality of components of the light returning from the focus point using a plurality of different light detectors and processing output signals from the plurality of light detectors to provide a plurality of co-registered images according to plural imaging modalities.

6. A method for imaging tissue, the method comprising:
   focusing a beam of light to a focus point;
   raster scanning the location of the focus point across a field of view in a vertical plane extending generally perpendicular to a surface of the tissue and collecting and detecting light returning from the focus point to provide a first xz plane image;
   scanning the location of the focus point in a y-direction transverse to the vertical plane to obtain a sequence of additional xz plane images corresponding to vertical planes parallel to and spaced apart in a y-direction from the vertical plane, the first xz plane image and the additional xz plane images constituting a set of xz plane images; and
   processing the set of xz plane images to provide volumetric image data for the tissue;

wherein focusing the beam of light comprises passing the light through an objective and raster scanning the location of the focus point comprises optically scanning the beam in an x direction in coordination with scanning the objective relative to the tissue along a z axis which is generally perpendicular to the x direction and to the surface of the tissue;

wherein processing the set of xz plane image frames comprises performing distortion compensation, the distortion compensation comprising monitoring an output of a z-axis position sensor to determine an actual trajectory of the objective during the scanning along the z axis and shifting pixels of the xz image according to the actual trajectory.

7. The method according to claim 6 wherein the scanning along the z axis is bidirectional, and the xz plane images include first xz plane images acquired while scanning the objective in a first direction along the z axis and second xz plane images acquired while scanning the objective in a second direction opposed to the first direction along the z axis.

8. The method according to claim 7 comprising monitoring the output of the z-axis position sensor to determine a first actual trajectory of the objective during the scanning along the z axis in the first direction and a second actual trajectory of the objective during the scanning along the z axis in the second direction and shifting the positions of the pixels of the first xz plane images in the z direction based on the first actual trajectory and shifting the pixels of the second xz plane images in the z direction based on the second actual trajectory.

9. A method for imaging tissue, the method comprising:
focusing a beam of light to a focus point;
raster scanning the location of the focus point across a field of view in a vertical plane extending generally perpendicular to a surface of the tissue and collecting and detecting light returning from the focus point to provide a first xz plane image;
scanning the location of the focus point in a y-direction transverse to the vertical plane to obtain a sequence of additional xz plane images corresponding to vertical planes parallel to and spaced apart in a y-direction from the vertical plane, the first xz plane image and the additional xz plane images constituting a set of xz plane images; and
processing the set of xz plane images to provide volumetric image data for the tissue;
wherein processing the set of xz plane image frames comprises performing motion compensation, the motion compensation comprising processing the xz plane images to determine representative z-axis locations of the tissue surface in each of the xz plane images and shifting the pixels of the xz plane images based on the representative z-axis locations.

10. The method according to claim 9 wherein shifting the pixels of the xz plane images based on the representative z-axis locations comprises determining differences between the representative z-axis locations for adjacent ones of a sequence of the xz plane images, for each of the xz plane images in the sequence calculating a cumulative difference of the representative z-axis locations relative to a selected one of the xz plane images and shifting the pixels of each of the xz plane images in the sequence by the corresponding cumulative difference.

11. The method according to claim 9 wherein the first xz plane image and the additional xz plane images constitute a first set of xz plane images for a first imaging modality and the method comprises acquiring one or more additional sets of xz plane images, each of the additional sets of xz plane images for a corresponding additional imaging modality and co-registered with the first set of xz plane images and the method comprises shifting the pixels of the xz plane images of the additional sets of xz plane images based on the representative z-axis locations determined for the first set of xz plane images.

12. A method for imaging tissue, the method comprising:
focusing a beam of light to a focus point;
raster scanning the location of the focus point across a field of view in a vertical plane extending generally perpendicular to a surface of the tissue and collecting and detecting light returning from the focus point to provide a first xz plane image;
scanning the location of the focus point in a y-direction transverse to the vertical plane to obtain a sequence of additional xz plane images corresponding to vertical planes parallel to and spaced apart in a y-direction from the vertical plane, the first xz plane image and the additional xz plane images constituting a set of xz plane images; and
processing the set of xz plane images to provide volumetric image data for the tissue;
wherein processing the set of xz plane image frames comprises performing surface flatting, wherein the surface flatting comprises:
processing the xz plane images to yield a 3D profile of the tissue surface;
smoothing the 3D profile of the tissue surface;
determining offsets corresponding to columns in the xz plane images that extend parallel to the z axis based on the smoothed 3D profile of the tissue surface; and
applying the offsets to the xz plane images.

13. The method according to claim 12 wherein the first xz plane image and the additional xz plane images constitute a first set of xz plane images for a first imaging modality and the method comprises acquiring one or more additional sets of xz plane images, each of the additional sets of xz plane images for a corresponding additional imaging modality and co-registered with the first set of xz plane images and the method comprises applying the offsets to the xz plane images of the additional sets of xz plane images.

14. Apparatus for imaging tissue, the apparatus comprising:
a laser light source operative to emit a beam of light;
an objective arranged to receive and focus the beam of light to a focus point;
a scanner unit in an optical path between the laser light source and the objective, the scanner unit operative to redirect the beam of light and thereby cause the focus point to scan in an x direction;
a z-axis scanner operative to move the objective in a z direction parallel to an optical axis of the objective,
a first light detector arranged to receive light returning through the objective from the focus point and to generate an output signal representing an intensity of the light returning,
a tissue stabilizing mechanism coupled to the objective by way of a movable stage operative to move tissue relative to the objective in a y direction that is transverse relative to the x direction while holding the objective fixed,
a controller configured to generate coordinated driving signals for the scanner unit and the z-axis scanner to cause the focus point to be raster scanned in an xz plane and control signals for the movable stage to cause the focus point to be scanned in the y direction, a frame grabber operative to monitor the output signal in coordination with the raster scanning of the focus point to build a first series of xz image frames, and a data processor connected to receive the xz image frames and configured to process the xz image frames to provide volumetric image data for a volume scanned by the focus point.

15. The apparatus according to claim 14 comprising:

a first wavelength selective element in the optical path between the scanning unit and the objective, the first wavelength selective element arranged to redirect a portion of the returning light having a wavelength that is shorter than a wavelength of the beam of light out of the beam and a second light detector arranged to detect light from the portion of the returning light; and a second wavelength selective element arranged to receive the portion of the returning light redirected by the first wavelength selective element and to split the portion of the returning light into first and second parts; and a third light detector arranged to detect light of the third part wherein the second light detector is arranged to detect light of the second part.

16. The apparatus according to claim 14 wherein a range of scanning in the y direction is at least three times larger than a range of scanning in the x direction.

17. Apparatus for imaging tissue, the apparatus comprising:

a laser light source operative to emit a beam of light;

an objective arranged to receive and focus the beam of light to a focus point;

a scanner unit in an optical path between the laser light source and the objective, the scanner unit operative to redirect the beam of light and thereby cause the focus point to scan in an x direction;

a z-axis scanner operative to move the objective in a z direction parallel to an optical axis of the objective, a first light detector arranged to receive light returning through the objective from the focus point and to generate an output signal representing an intensity of the light returning, a tissue stabilizing mechanism coupled to the objective by way of a movable stage operative to move tissue relative to the objective in a y direction that is transverse relative to the x direction, a controller configured to generate coordinated driving signals for the scanner unit and the z-axis scanner to cause the focus point to be raster scanned in an xz plane and control signals for the movable stage to cause the focus point to be scanned in the y direction, a frame grabber operative to monitor the output signal in coordination with the raster scanning of the focus point to build a first series of xz image frames, and a data processor connected to receive the xz image frames and configured to process the xz image frames to provide volumetric image data for a volume scanned by the focus point;

a first wavelength selective element in the optical path between the scanning unit and the objective, the first wavelength selective element arranged to redirect a portion of the returning light having a wavelength that is shorter than a wavelength of the beam of light out of the beam and a second light detector arranged to detect light from the portion of the returning light; and a second wavelength selective element arranged to receive the portion of the returning light redirected by the first wavelength selective element and to split the portion of the returning light into first and second parts; and a third light detector arranged to detect light of the third part wherein the second light detector is arranged to detect light of the second part;

wherein an output of the third light detector is connected to the frame grabber and the frame grabber is configured to build a third series of xz image frames co-registered with the first series of xz image frames and an output of the second light detector is connected to the frame grabber and the frame grabber is configured to build a second series of xz image frames co-registered with the first series of xz image frames.

18. Apparatus for imaging tissue, the apparatus comprising:

a laser light source operative to emit a beam of light;

an objective arranged to receive and focus the beam of light to a focus point;

a scanner unit in an optical path between the laser light source and the objective, the scanner unit operative to redirect the beam of light and thereby cause the focus point to scan in an x direction;

a z-axis scanner operative to move the objective in a z direction parallel to an optical axis of the objective, a first light detector arranged to receive light returning through the objective from the focus point and to generate an output signal representing an intensity of the light returning, a tissue stabilizing mechanism coupled to the objective by way of a movable stage operative to move tissue relative to the objective in a y direction that is transverse relative to the x direction, a controller configured to generate coordinated driving signals for the scanner unit and the z-axis scanner to cause the focus point to be raster scanned in an xz plane and control signals for the movable stage to cause the focus point to be scanned in the y direction, a frame grabber operative to monitor the output signal in coordination with the raster scanning of the focus point to build a first series of xz image frames, and a data processor connected to receive the xz image frames and configured to process the xz image frames to provide volumetric image data for a volume scanned by the focus point; and a z-axis position sensor operative to output a signal indicative of a displacement of the objective in the z direction wherein the processing the set of xz plane image frames comprises performing distortion compensation, the distortion compensation comprising monitoring the output of the z-axis position sensor to determine an actual trajectory of the objective during the scanning along the z axis and shifting pixels of the xz image frames according to the actual trajectory.

19. The apparatus according to claim 18 wherein the scanning along the z axis is bidirectional, the xz plane image frames include first xz plane image frames acquired while scanning the objective in a first direction along the z axis and second xz plane image frames acquired while scanning the objective in a second direction opposed to the first direction along the z axis.

20. The apparatus according to claim 18 wherein the data processor is configured to monitor the output of the z-axis position sensor to determine a first actual trajectory of the objective during the scanning along the z axis in the first direction and a second actual trajectory of the objective during the scanning along the z axis in the second direction and to shift the positions of the pixels of the first xz plane image frames in the z direction based on the first actual trajectory and to shift the pixels of the second xz plane images in the z direction based on the second actual trajectory.

21. Apparatus for imaging tissue, the apparatus comprising:
   a laser light source operative to emit a beam of light;
   an objective arranged to receive and focus the beam of light to a focus point;
   a scanner unit in an optical path between the laser light source and the objective, the scanner unit operative to redirect the beam of light and thereby cause the focus point to scan in an x direction;
   a z-axis scanner operative to move the objective in a z direction parallel to an optical axis of the objective,
   a first light detector arranged to receive light returning through the objective from the focus point and to generate an output signal representing an intensity of the light returning,
   a tissue stabilizing mechanism coupled to the objective by way of a movable stage operative to move tissue relative to the objective in a y direction that is transverse relative to the x direction,
   a controller configured to generate coordinated driving signals for the scanner unit and the z-axis scanner to cause the focus point to be raster scanned in an xz plane and control signals for the movable stage to cause the focus point to be scanned in the y direction,
   a frame grabber operative to monitor the output signal in coordination with the raster scanning of the focus point to build a first series of xz image frames, and
   a data processor connected to receive the xz image frames and configured to process the xz image frames to provide volumetric image data for a volume scanned by the focus point;
   wherein the data processor is configured to perform motion compensation, the motion compensation comprising processing the xz plane image frames to determine representative z-axis locations of a tissue surface in each of the xz plane images and to shift the pixels of the xz plane images based on the representative z-axis locations.

22. The apparatus according to claim 21 wherein the data processor is configured to determine differences between the representative z-axis locations for adjacent ones of a sequence of the xz plane image frames, for each of the xz plane image frames in the sequence calculating a cumulative difference of the representative z-axis locations relative to a selected one of the xz plane images and shifting the pixels of each of the xz plane image frames in the sequence by the corresponding cumulative difference.

* * * * *